(12) United States Patent
Isenberg et al.

(10) Patent No.: US 10,780,240 B2
(45) Date of Patent: *Sep. 22, 2020

(54) ORAL AIRWAYS

(71) Applicant: Isen Innovations, LLC, Wilmington, NC (US)

(72) Inventors: Amy Isenberg, Wilmington, NC (US); Chris Hoy, Charlotte, NC (US)

(*) Notice: Subject to any disclaimer, the term of this patent is extended or adjusted under 35 U.S.C. 154(b) by 443 days.

This patent is subject to a terminal disclaimer.

(21) Appl. No.: 15/614,069

(22) Filed: Jun. 5, 2017

(65) Prior Publication Data

US 2017/0266402 A1 Sep. 21, 2017

Related U.S. Application Data

(63) Continuation of application No. 14/444,878, filed on Jul. 28, 2014, now Pat. No. 9,669,174, which is a continuation of application No. 11/967,188, filed on Dec. 29, 2007, now abandoned, which is a continuation of application No. 11/767,473, filed on Jun. 22, 2007, now Pat. No. 7,866,313.

(60) Provisional application No. 60/883,116, filed on Jan. 2, 2007.

(51) Int. Cl.
*A61M 16/04* (2006.01)
*A61B 1/00* (2006.01)
*A61B 1/267* (2006.01)

(52) U.S. Cl.
CPC ..... *A61M 16/0488* (2013.01); *A61B 1/00105* (2013.01); *A61B 1/00154* (2013.01); *A61B 1/00165* (2013.01); *A61B 1/2673* (2013.01); *A61M 16/049* (2014.02); *A61M 16/0493* (2014.02); *A61M 16/0495* (2014.02); *A61M 2205/02* (2013.01); *A61M 2210/1028* (2013.01)

(58) Field of Classification Search
CPC .......................................... A61M 16/04–0468
See application file for complete search history.

(56) References Cited

U.S. PATENT DOCUMENTS

| 3,930,507 A | * | 1/1976 | Berman | ................... | A61B 1/24 |
| | | | | | 128/207.14 |
| 4,068,658 A | * | 1/1978 | Berman | ............ | A61M 16/0488 |
| | | | | | 128/200.26 |

(Continued)

*Primary Examiner* — LaToya M Louis
(74) *Attorney, Agent, or Firm* — Chad D. Tillman; Jeremy C. Doerre; Tillman Wright PLLC

(57) ABSTRACT

An oral airway includes a first component having a first guiding surface and a second component having a second guiding surface. The first component and the second component are adapted to be removably coupled together such that the first guiding surface and the second guiding surface collectively define and encompass an interior passage through the oral airway that is dimensioned to direct, for example, a fiber-optic scope or an endotracheal tube extending through the interior passage for tracheal intubation. The first and second components are configured to be decoupled and independently removed from a patient's mouth without disrupting an endotracheal tube that has been extended through the conduit for tracheal intubation. The first and second components may be maintained in coupled disposition by an interlocking mechanical structure. The first and second components also may be maintained in coupled disposition by magnetism.

17 Claims, 23 Drawing Sheets

(56) References Cited

U.S. PATENT DOCUMENTS

| | | | | |
|---|---|---|---|---|
| 4,640,273 A | * | 2/1987 | Greene | A61B 1/24 128/207.14 |
| 5,069,206 A | * | 12/1991 | Crosbie | A61M 25/02 128/200.26 |
| 5,464,011 A | * | 11/1995 | Bridge | A61M 16/04 128/200.26 |
| 7,534,228 B2 | * | 5/2009 | Williams | A61M 25/02 128/200.24 |
| 2003/0075184 A1 | * | 4/2003 | Persichetti | A63B 71/085 128/861 |
| 2006/0213512 A1 | * | 9/2006 | Takuma | A61M 16/0488 128/200.26 |
| 2007/0089740 A1 | * | 4/2007 | Baumert | A63B 23/18 128/203.12 |

* cited by examiner

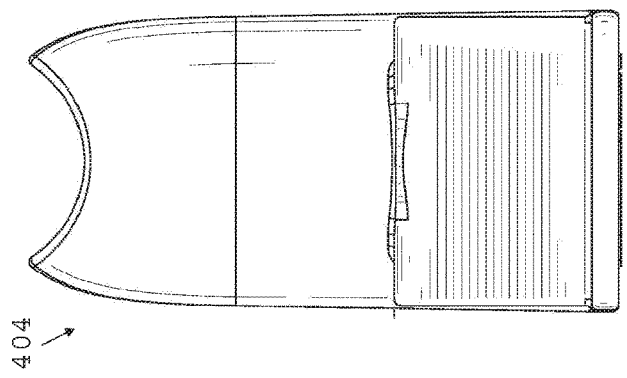
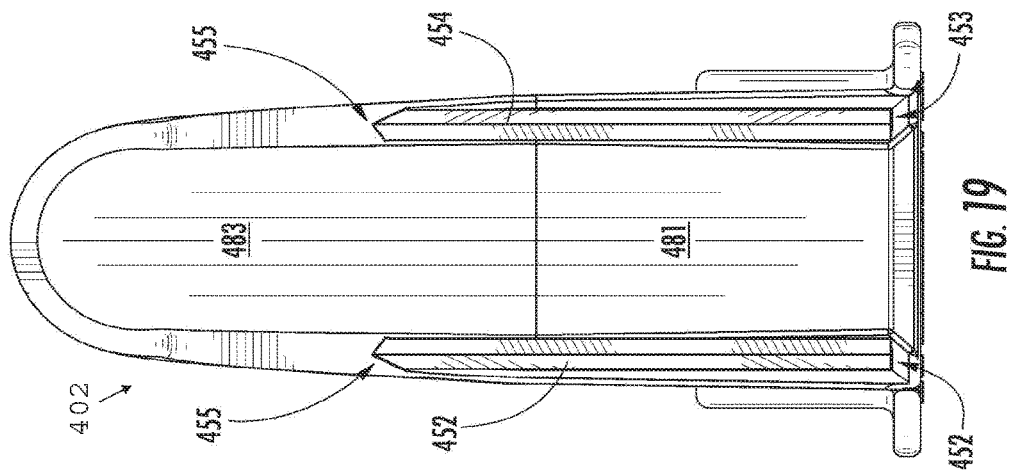

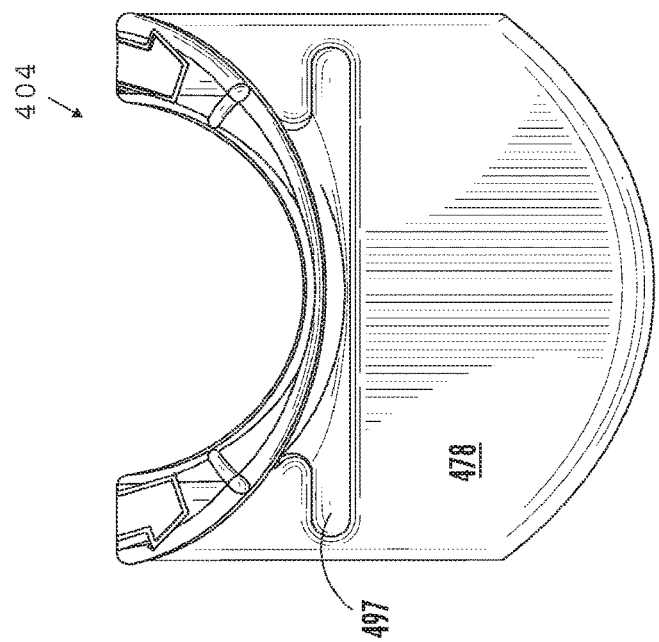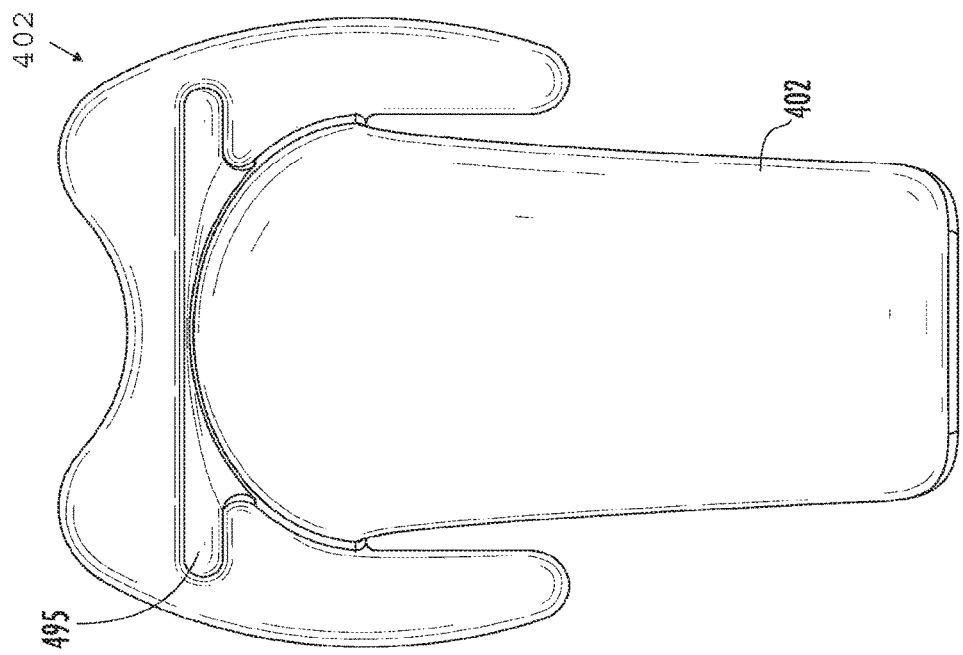

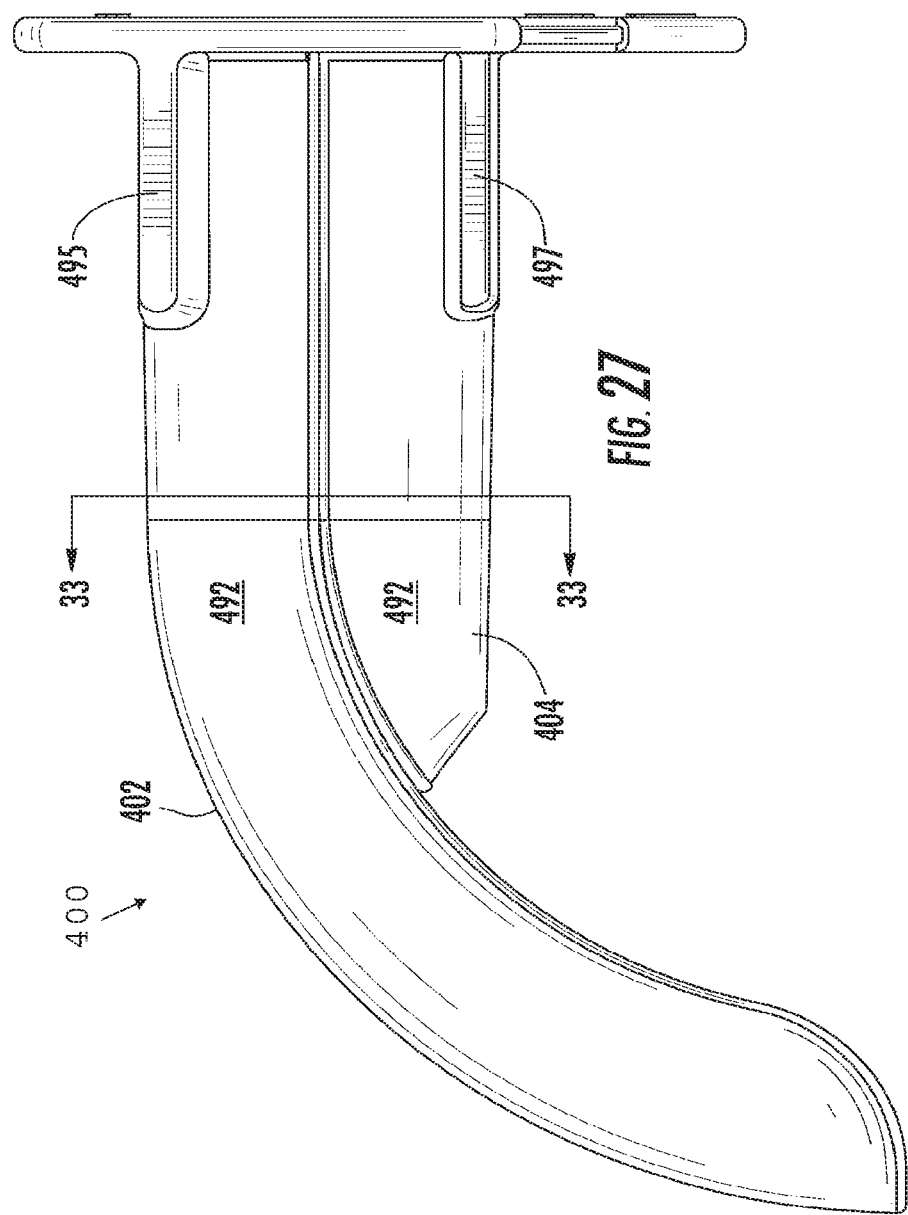

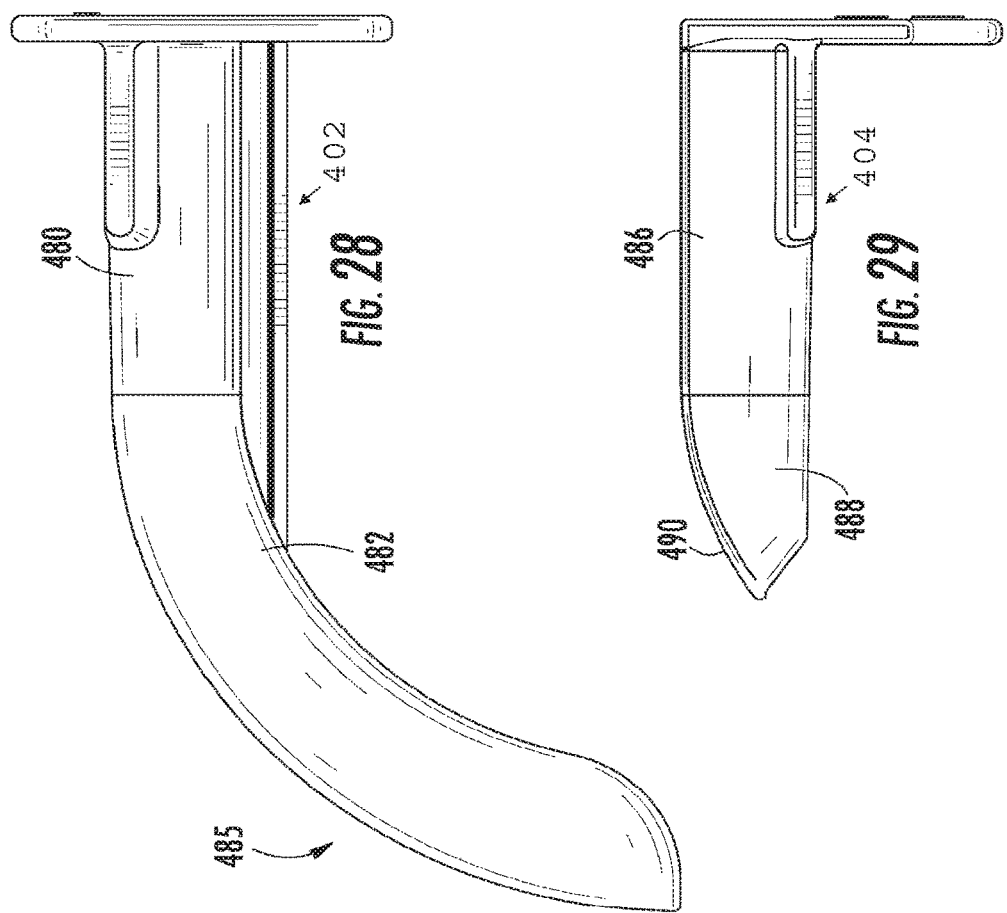

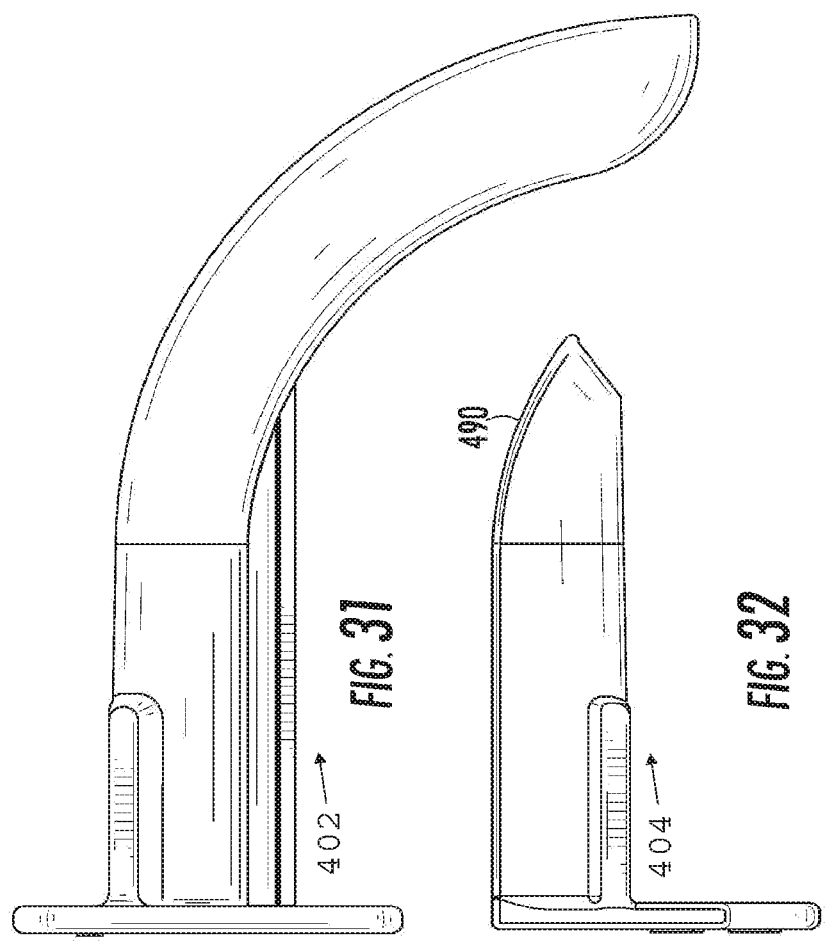

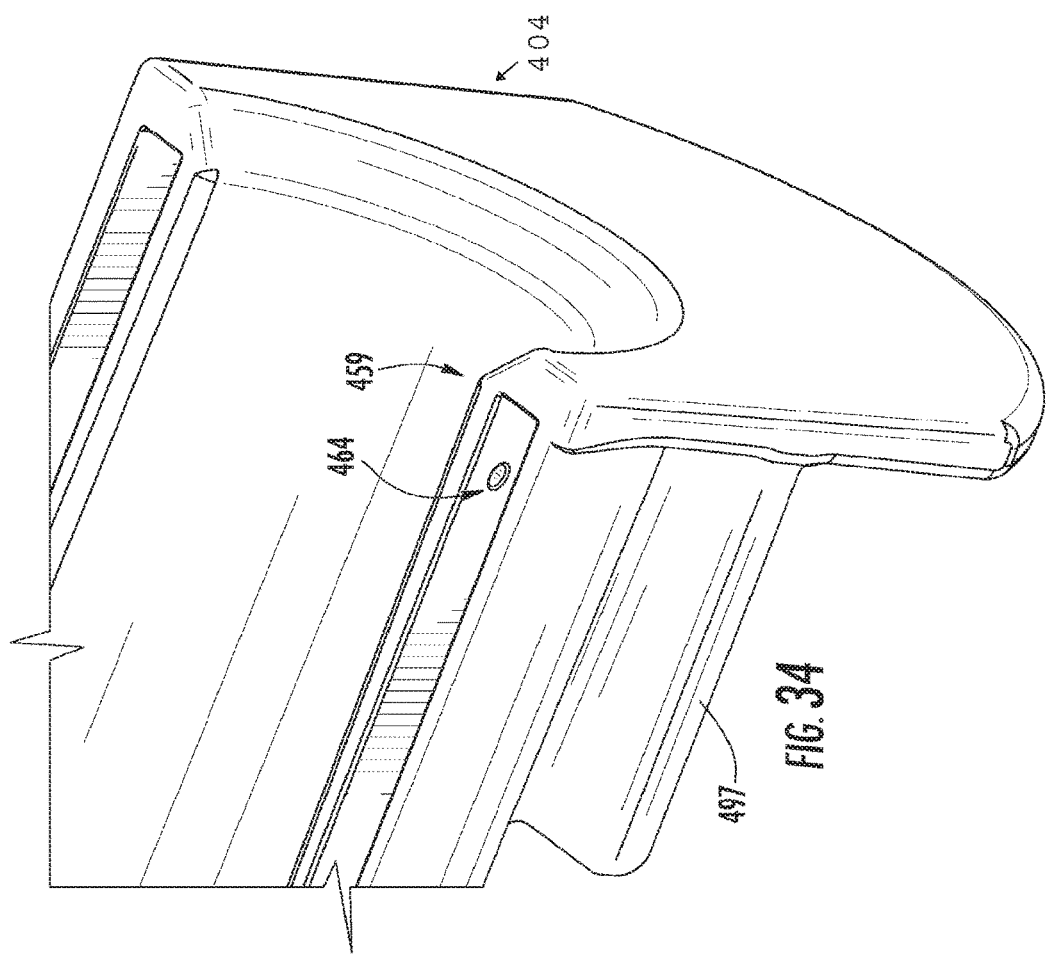

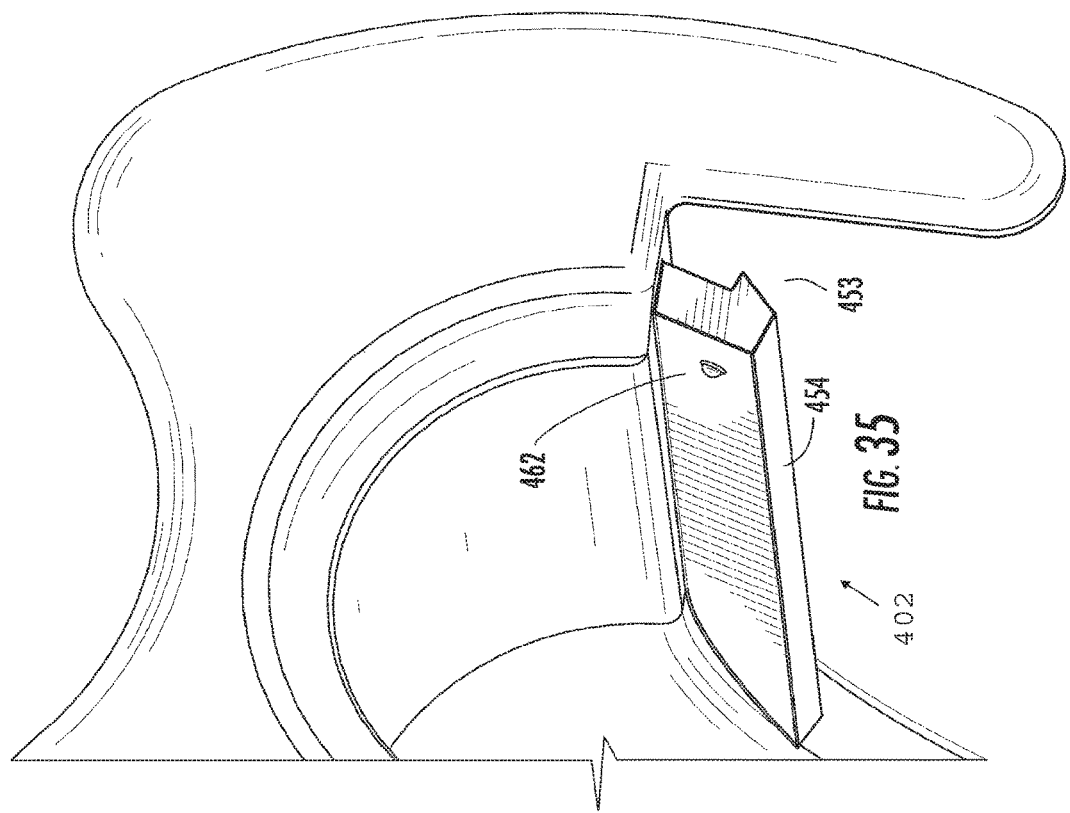

ORAL AIRWAYS

CROSS REFERENCE TO RELATED APPLICATIONS

The present application is a U.S. continuation patent application of, and claims priority under 35 U.S.C. § 120 to, U.S. nonprovisional patent application Ser. No. 14/144,878, filed Jul. 28, 2014, which nonprovisional patent application is incorporated by reference herein, and which '878 application is a U.S. continuation patent application of, and claims priority under 35 U.S.C. § 120 to, U.S. nonprovisional patent application Ser. No. 11/967,188, filed Dec. 29, 2007, which nonprovisional patent application is incorporated by reference herein, and which '188 application is a U.S. continuation patent application of, and claims priority under 35 U.S.C. § 120 to, U.S. nonprovisional patent application Ser. No. 11/767,473, filed Jun. 22, 2007, which nonprovisional patent application is incorporated by reference herein, and which '473 application is a U.S. nonprovisional patent application of, and claims priority under 35 U.S.C. § 119(e) to, U.S. provisional patent application Ser. No. 60/883,116, filed Jan. 2, 2007, which provisional patent application is incorporated by reference herein, and which '188 application further is a U.S. nonprovisional patent application of, and claims priority under 35 U.S.C. § 119(e) to, U.S. provisional patent application Ser. No. 60/883,116, filed Jan. 2, 2007.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The invention generally relates to oral airways and, in particular to oral airways that facilitate fiber-optic intubation of the trachea.

Oral airways are well known. Generally, an oral airway is a device used in anesthesia to maintain patency of the path from the mouth of a patient to the pharynx of the patient. Oral airways are commonly utilized in mask ventilation for CPR or induction of anesthesia.

One use of oral airways is to facilitate fiber-optic intubation of the trachea with an endotracheal tube. The oral airway splints open the teeth providing a conduit through which a thin filamentous fiber-optic bronchoscope may be passed from the mouth through the vocal cords so that, in turn, an endotracheal tube may be passed over the fiber-optic scope through the oral airway to the proper position through the vocal cords. Such technique is sometimes known as the "Seldinger" technique.

The basic design of conventional oral airways in use today is that of a hollow plastic tube which, when placed between the teeth as a bite block, follows a natural curve to the posterior pharynx to pull the tongue forward to facilitate passage of a fiber-optic tube bronchoscope to the larynx and through the vocal cords.

Each of the following U.S. patent references discloses conventional oral airways: Ovassapian U.S. Pat. No. 5,024,218; Williams U.S. Pat. No. 4,338,930; Berman U.S. Pat. Nos. 4,067,331, 4,054,135, and 3,930,507; Northway-Meyer U.S. Pat. No. 4,848,331; and Alfery U.S. Patent Application Publication No. 2003/0000534. Each of these U.S. patent references is hereby incorporated herein by reference.

Currently available commercial products that are believed to be based on the Ovassapian, Berman, and Williams patented oral airways discussed above are illustrated in FIGS. 1-4.

FIGS. 1 and 2 are a top and side perspective view, respectively, of a commercially available oral airway 10 believed to represent the Ovassapian oral airway. As shown therein, the airway 10 includes a wide, flat lingual surface 12 that allows for stability of the oral airway and forward depression of the tongue, both of which increase the ease of positioning the fiber-optic scope. The construction of this oral airway 10 is perhaps best illustrated in the incorporated reference U.S. Pat. No. 5,024,218. Unfortunately, the oral airway 10 has been found to tend to direct the fiber-optic scope and endotracheal tube posteriorly toward the esophagus rather than anteriorly toward the trachea. The oral airway 10 also has been found to be very difficult to remove without disrupting placement of an endotracheal tube after the endotracheal tube has been properly positioned with respect to the trachea.

With reference to FIG. 3, a commercially available oral airway 20 believed to represent the Williams oral airway is shown and includes a posterior pharyngeal curve 22 that tends to direct a fiber-optic scope and endotracheal tube anteriorly toward the trachea. The construction of this oral airway 10 is perhaps best illustrated in the incorporated reference U.S. Pat. No. 4,338,930. Unfortunately, the oral airway 20 has been found to be very narrow and to wobble in a patient's mouth, thereby making the fiber-optic scoping process difficult. The oral airway 20 also has been found to be cumbersome to remove without disrupting placement of an endotracheal tube after the endotracheal tube has been properly positioned with respect to the trachea.

Finally, with reference to FIG. 4, a commercially available oral airway 30 believed to represent the Berman oral airway is shown and includes, on one side, a sidewall having a first opening or cutaway section (not shown) that extends the entire length of the oral airway 30 and, on the other side as shown, a sidewall having a second opening or cutaway section 32 that generally extends along the midsection of the oral airway 30, with the sidewall further including hinging sections 35 disposed there along. The hinging sections 35 permit the opening of the oral airway, i.e., expansion of the first opening or cutaway extending the entire length of the oral airway 30, for easy removal of a fiber-optic scope or endotracheal tube. While permitting hinging movement, the hinging sections 35 nevertheless continuously join the oral airway 30 such that the oral airway 30 is considered to be a single integral unit. The construction of this oral airway 30 is perhaps best illustrated in the incorporated reference U.S. Pat. No. 4,054,135. Unfortunately, the oral airway 30 has been found to be very narrow and unstable and to include a posterior curve that tends to direct a fiber-optic scope and endotracheal tube posteriorly toward the esophagus instead of anteriorly toward the trachea.

Even in view of the conventional oral airways, it is believed that a need exists for still yet further improvement in oral airways used to facilitate fiber-optic intubation of the trachea.

SUMMARY OF THE INVENTION

The invention includes many aspects and features. Moreover, while many aspects and features relate to, and are described in, the context of oral airways that facilitate fiber-optic intubation of the trachea, the invention is not limited to such use of oral airways and may be used in other contexts as well.

In an aspect of the invention, an oral airway includes first and second components that are removably coupled together to define a conduit configured to receive therethrough a fiber-optic scope or an endotracheal tube for intubation of the trachea of a patient. Furthermore, the first and second components are configured to be decoupled and independently removed from a patient's mouth without disrupting an endotracheal tube that has been received through the conduit for tracheal intubation.

In a feature of the invention, the first and second components are maintained in coupled disposition by an interlocking mechanical structure. The interlocking mechanical structure may include one or more spring-like elements and/or may include one or more detents.

In a feature of the invention, the oral airway further includes a latch mechanism. In this respect, the first and second components, when removably coupled together, are retained in physical engagement with one another by the latch mechanism.

In a feature of the invention, the first component includes elastic, spring-like arms that extend from and form part of the first component, and the second component includes sidewalls having corresponding slots formed therein. Furthermore, detents are formed in the arms of the first component and are received and retained by corresponding depressions formed in the slots of the second component.

In a feature of the invention, the first component includes first and second tongues extending in generally parallel relation, the second component includes first and second grooves extending in generally parallel relation, and, when the first and second components are removably coupled together, the first and second tongues extend, respectively, within the first and second grooves in interlocking engagement. Optionally, in connection with this feature, each tongue is elongate and includes a leading end and a trailing end; each groove is elongate and includes an opening at a forward end for receiving the leading end of a respective tongue therethrough; and, when the first and second components are removably coupled together for facilitating tracheal intubation, the elongate tongues are received within the elongate grooves. Each tongue further may include a protuberance proximate the leading end; each groove further may include a recess located proximate a rear end; and, when the first and second components are removably coupled together for facilitating tracheal intubation, the protuberances of the tongues at the leading ends thereof then may be received within the recesses of the grooves at the rear ends thereof for latching of the first and second components in physical engagement with one another. Each groove may include a T slot or an L slot.

In a feature of the invention, the first and second components are maintained in their coupled disposition by magnetism. In this regard, the first component may include sidewalls having first magnetized elements and the second component may include sidewalls having second magnetized elements that respectively attract the first magnetized elements when the first and second components are coupled together.

In a feature of the invention, the oral airway further includes a mouth guard for abutting the exterior area of the mouth of a patient during endotracheal intubation. The mouth guard prevents the oral airway from overextending into the mouth of the patient. In connection therewith, the first component and the second component may define a chamfer between the interior passage through the oral airway and an exterior surface of the mouth guard; the first component may form a first mouth guard portion and the second component may form a second mouth guard portion, with the first mouth guard portion and the second mouth guard portion defining the mouth guard itself. Still further, the first mouth guard portion and the second mouth guard portion each may have surfaces that extend in generally coplanar relation for presenting a flush exterior mouth guard surface of the oral airway; the first mouth guard portion may extend adjacent opposite lateral sides of the second mouth guard portion; and/or the second mouth guard portion further may include an area dimensioned for grasping the second component for decoupling of the first and second components.

In another aspect of the invention, an oral airway includes a first component having a first guiding surface and a second component having a second guiding surface. Furthermore, the first component and the second component are adapted to be removably coupled together such that the first guiding surface and the second guiding surface collectively define and encompass an interior passage through the oral airway that is dimensioned to direct a fiber-optic scope or an endotracheal tube extending through the interior passage for tracheal intubation.

In a feature of this aspect, the first component further includes a posterior curve that directs a fiber-optic scope or endotracheal tube anteriorly toward the vocal cords during tracheal intubation.

In a feature of this aspect, the first and second components are configured to be decoupled and independently removed from a patient's mouth without disrupting an endotracheal tube that has been extended through the conduit for tracheal intubation.

In a feature of this aspect, the interior passage is generally oval in cross-sectional profile, and the interior passage may be generally circular in cross-sectional profile.

In a feature of this aspect, the first and second components provide a continuous, uninterrupted exterior surface circumferentially surrounding the interior passage. Additionally, the exterior surface may be generally oval in cross-sectional profile. The first component also may include a first generally planar member protracting on opposite lateral sides of the first component, and the second component may include a second generally planar member protracting on opposite lateral sides of the second component, with the first generally planar member and the second generally planar member extending in spaced, generally parallel relation to one another. The first generally planar member and the second generally planar member thereby may be configured to splint the teeth of the mouth of a patient, and provide stability against rotation of the oral airway, during endotracheal intubation. The second generally planar member also may include a flat lingual surface that is configured to forwardly depress the tongue of a patient during endotracheal intubation.

In a feature of this aspect, the second component includes tapering side edges.

In a feature of this aspect, the first and second components are maintained in coupled disposition by an interlocking mechanical structure.

In a feature of this aspect, the first component is configured to slide out of physical engagement with the second component.

In a feature of this aspect, when the first component and the second component are removably coupled together, the oral airway further includes a mouth guard for abutting the exterior area of the mouth of a patient during endotracheal intubation and preventing the oral airway from overextending into the mouth of the patient. The first component and the second component, when removably coupled together, also may define a chamfer between the interior passage through the oral airway and an exterior surface of the mouth guard. When removably coupled together, the first component also may form a first mouth guard portion and wherein the second component forms a second mouth guard portion, the first mouth guard portion and the second mouth guard portion defining the mouth guard itself. Additionally, the first mouth guard portion and the second mouth guard portion each may have surfaces that extend in generally coplanar relation for presenting a flush exterior mouth guard surface of the oral airway when the first component and the second component are removably coupled together; the first mouth guard portion may extend adjacent opposite lateral sides of the second mouth guard portion when the first component and the second component are removably coupled together; and the second mouth guard portion further may include an area dimensioned for grasping by hand of the second component for decoupling of the first and second components.

In a feature of this aspect, the first and second components are maintained in coupled disposition by an interlocking mechanical structure. The interlocking mechanical structure may include a spring-like element and/or a detent.

In a feature of this aspect, the oral airway further includes a latch mechanism. Furthermore, the first and second components, when removably coupled together, are retained in physical engagement with one another by the latch mechanism.

In a feature of this aspect, the first component includes first and second tongues extending in generally parallel relation, wherein the second component includes first and second grooves extending in generally parallel relation, and wherein, when the first and second components are removably coupled together, the first and second tongues extend, respectively, within the first and second grooves in interlocking engagement. Additionally, each tongue may be elongate and include a leading end and a trailing end; each groove may be elongate and include an opening at a forward end for receiving the leading end of a respective tongue therethrough; and, when the first and second components are removably coupled together for facilitating tracheal intubation, the elongate tongues may be received within the elongate grooves. Each tongue may further include a protuberance proximate the leading end; each groove further may include a recess located proximate a rear end; and, when the first and second components are removably coupled together for facilitating tracheal intubation, the protuberances of the tongues at the leading ends thereof may then be received within the recesses of the grooves at the rear ends thereof for latching of the first and second components in physical engagement with one another. Each groove also may include a T slot or an L slot.

In a feature of this aspect, the first and second components are maintained in their coupled disposition by magnetism. The first component may include sidewalls having first magnetized elements and the second component may include sidewalls having second magnetized elements that respectively attract the first magnetized elements when the first and second components are coupled together.

In another aspect of the invention, an oral airway includes superior and inferior components removably coupled together. Additionally, the superior component has an anterior portion that extends generally linearly in a longitudinal direction a first extent and includes a first curved surface; and a posterior elbow portion that extends generally curvilinearly in the longitudinal direction and includes a second curved surface. Furthermore, the second curved surface of the elbow portion in combination with the first curved surface of the anterior portion defines a first guiding surface of the oral airway. The inferior component has a first portion that extends generally linearly in the longitudinal direction approximately the first extent, and the first portion of the inferior component includes a first curved surface that is located in opposing relation to the first curved surface of the anterior portion of the superior component. A second portion of the inferior component includes a second curved surface that is located in opposing relation to the second curved surface of the elbow portion. The first and second curved surfaces of the first and second portions of the inferior component collectively define a second guiding surface. The first guiding surface and the second guiding surface collectively define and encompass an interior passage through the oral airway that is dimensioned to direct a fiber-optic scope or an endotracheal tube extending through the interior passage for tracheal intubation.

In a feature of this aspect, the second curved surface of the elbow portion includes a posterior curve that directs a fiber-optic scope or endotracheal tube toward the vocal cords during tracheal intubation.

In a feature of this aspect, the superior and inferior components are configured to be decoupled and independently removed from a patient's mouth without disrupting an endotracheal tube that has been extended through the conduit for tracheal intubation.

In a feature of this aspect, the interior passage is generally oval in cross-sectional profile and may be generally circular in cross-sectional profile.

In a feature of this aspect, the superior and inferior components provide a continuous, uninterrupted exterior surface that circumferentially surrounds the interior passage. The exterior surface may be generally oval in cross-sectional profile. Furthermore, the superior component may include a first generally planar member that protracts in opposite lateral directions from the exterior surface of the anterior portion of the superior component, and the inferior component may likewise include a second generally planar member protracting in opposite lateral directions from the exterior surface of the first portion of the inferior component, with the first generally planar member and the second generally planar member extending in spaced parallel relation to one another. The first generally planar member and the second generally planar member thereby may be configured to splint the teeth of the mouth of a patient, and provide stability against rotation of the oral airway, during endotracheal intubation. The second generally planar member also may include a flat lingual surface that is configured to forwardly depress the tongue of a patient during endotracheal intubation.

In a feature of this aspect, the second portion of the inferior component includes tapering side edges.

In a feature of this aspect, the superior and inferior components are maintained in coupled disposition by an interlocking mechanical structure.

In a feature of this aspect, the inferior component is configured to slide out of physical engagement with the superior component.

In a feature of this aspect, the oral airway further includes a mouth guard for abutting the exterior area of the mouth of a patient during endotracheal intubation and for preventing the oral airway from overextending into the mouth of the patient. The anterior portion of the superior component and the first portion of the inferior component further may define a chamfer between the interior passage through the oral airway and an exterior surface of the mouth guard. The superior component also may form a first mouth guard portion and the inferior component may form a second mouth guard portion, with the first mouth guard portion and the second mouth guard portion defining the mouth guard itself.

Additionally, the first mouth guard portion and the second mouth guard portion each may have surfaces that extend in generally coplanar relation for presenting a flush exterior mouth guard surface of the oral airway; the first mouth guard portion may extend adjacent opposite lateral sides of the second mouth guard portion; and the second mouth guard portion further may include an area dimensioned for grasping by the hand for decoupling of the superior and inferior components.

In another aspect of the invention, an oral airway includes first and second components that are removably coupled together to define a conduit through which a fiber-optic scope and/or an endotracheal tube may be extended, the first and second components completely encircling such fiber-optic scope or endotracheal tube when extending through the conduit. Additionally, when decoupled, the first and second components are independently removable from a patient's mouth without disrupting placement of an endotracheal tube.

In a feature of this aspect, the first and second components are maintained in coupled disposition by an interlocking mechanical structure. The interlocking mechanical structure may include an elastic element and/or may include a detent.

In a feature of this aspect, the first and second components are maintained in coupled disposition by magnetism.

In a feature of this aspect, the first and second components, when coupled together, define a wide, flat lingual surface that allows for stability of the oral airway and forward depression of the tongue when placed within a patient's mouth.

In a feature of this aspect, the oral airway further includes a posterior curve defined by one or both of the first and second components that directs the fiber-optic scope and endotracheal tube anteriorly toward the vocal cords.

In a feature of this aspect, the oral airway further includes a posterior curve defined by one or both of the first and second components that directs the fiber-optic scope and endotracheal tube anteriorly toward the vocal cords.

In still other aspects of the invention, methods for fiber-optic intubation of the trachea include the use of oral airways in accordance with any of the foregoing aspects.

In accordance with a particular one of these aspects, a method of tracheal intubation includes the steps of extending an endotracheal tube through a conduit defined by first and second components of an oral airway, wherein the first and second components are removably coupled together to define the conduit; decoupling the first and second components after an endotracheal tube has been extended through the conduit for tracheal intubation such that the first and second components are physically separated from one another; removing the first component from the patient's mouth without disrupting the endotracheal tube; and removing the second component from the patient's mouth without disrupting the endotracheal tube.

In a feature of this aspect, the step of removing the first component is performed prior to the step of removing the second component.

In a feature of this aspect, the step of removing the first component is performed after the step of removing the second component.

In a feature of this aspect, the first and second components completely encompass the endotracheal tube when extended through the conduit.

In a feature of this aspect, the step of decoupling the first and second components includes sliding one of the components relative to the other of the components.

In a feature of this aspect, the step of decoupling the first and second components includes further applying a sufficient amount of force to overcome a latch that serves to retain the first and second components together in fixed disposition.

In still additional features of the invention, an oral airway may adapted, configured, or manufactured to provide a desirable smell and/or taste. For example, a flavoring material may be applied during the manufacture of the oral airway, or may be applied afterwards, that results in a desirable flavor being experienced when the oral airway is utilized in the mouth. The flavor may be, for example, that of a food, a natural flavor, or an artificial flavor including, but not limited to, bubble gum or a fruit, such as an orange. Alternatively, or in addition, a material may be may be applied during the manufacture of the oral airway, or may be applied afterwards, that results in a desirable scent or odor being experienced when the oral airway is utilized. The scent or odor may be that of a food or other pleasant item. In connection with the flavoring and/or scent, the oral airway may include a corresponding color, such as a pink color if the flavoring and/or scent is that of bubble gum.

In addition to the aforementioned aspects and features of the invention, it should be noted that the invention further encompasses the various possible combinations of such aspects and features.

BRIEF DESCRIPTION OF THE DRAWINGS

One or more preferred embodiments of the invention now will be described in detail with reference to the accompanying drawings, wherein the same general elements are referred to with the same or similar reference numerals.

FIG. 19 is a bottom plan view of the first component 402 of the oral airway of FIG. 11.

FIG. 20 is a bottom plan view of the second component 404 of the oral airway of FIG. 11.

FIG. 25 is a rear elevational view of the first component 402 of the oral airway of FIG. 11.

FIG. 26 is a rear elevational view of the second component 404 of the oral airway of FIG. 11.

FIG. 27 is first side elevational view of the oral airway 400 of FIG. 11.

FIG. 28 is a first side elevational view of the first component 402 of the oral airway of FIG. 11.

FIG. 29 is a first side elevational view of the second component 404 of the oral airway of FIG. 11.

FIG. 31 is a second side elevational view of the first component 402 of the oral airway of FIG. 11.

FIG. 32 is a second side elevational view of the second component 404 of the oral airway of FIG. 11.

FIG. 34 is a partial view of the second component 404 of the oral airway of FIG. 11 illustrating an indentation or recess 464 of the latch mechanism of the oral airway.

FIG. 35 is a partial view of the first component 402 of the oral airway of FIG. 11 illustrating raised bump or protuberance 462 of the latch mechanism of the oral airway.

DETAILED DESCRIPTION

Figure 2:
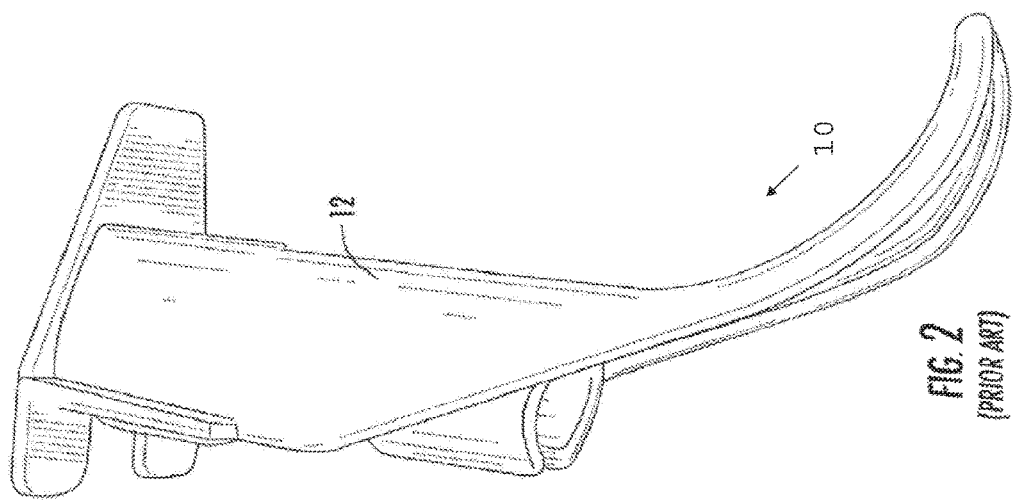
FIG. 2 is a perspective view of the side of the Ovassapian oral airway of FIG. 1.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Moreover, many embodiments, such as adaptations, variations, modifications, and equivalent arrangements, will be implicitly disclosed by the embodiments described herein and fall within the scope of the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more oral airways in accordance with one or more preferred embodiments of the invention are next described. The following description of such oral airways is merely exemplary in nature and is in no way intended to limit the invention, its applications, or uses.

Figure 1:
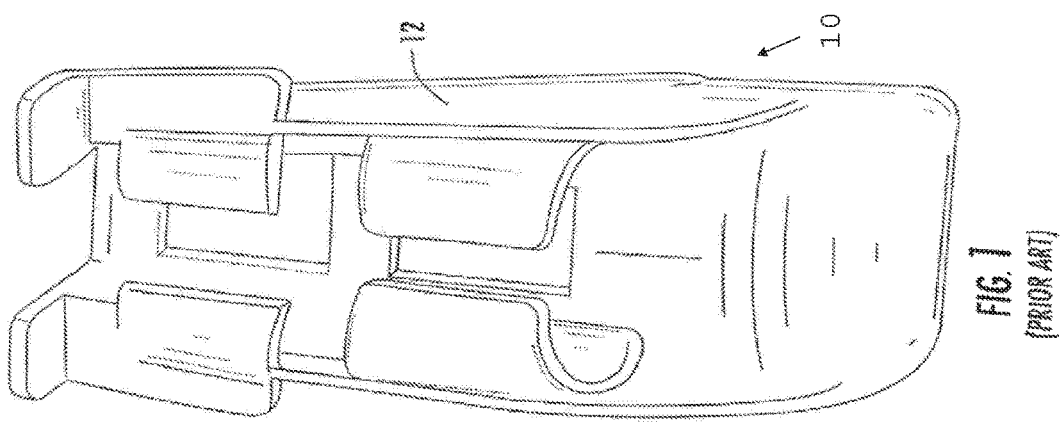
FIG. 1 is a perspective view of the top of a commercially available oral airway that is believed to be representative of the Ovassapian oral airway.
Figure 3:
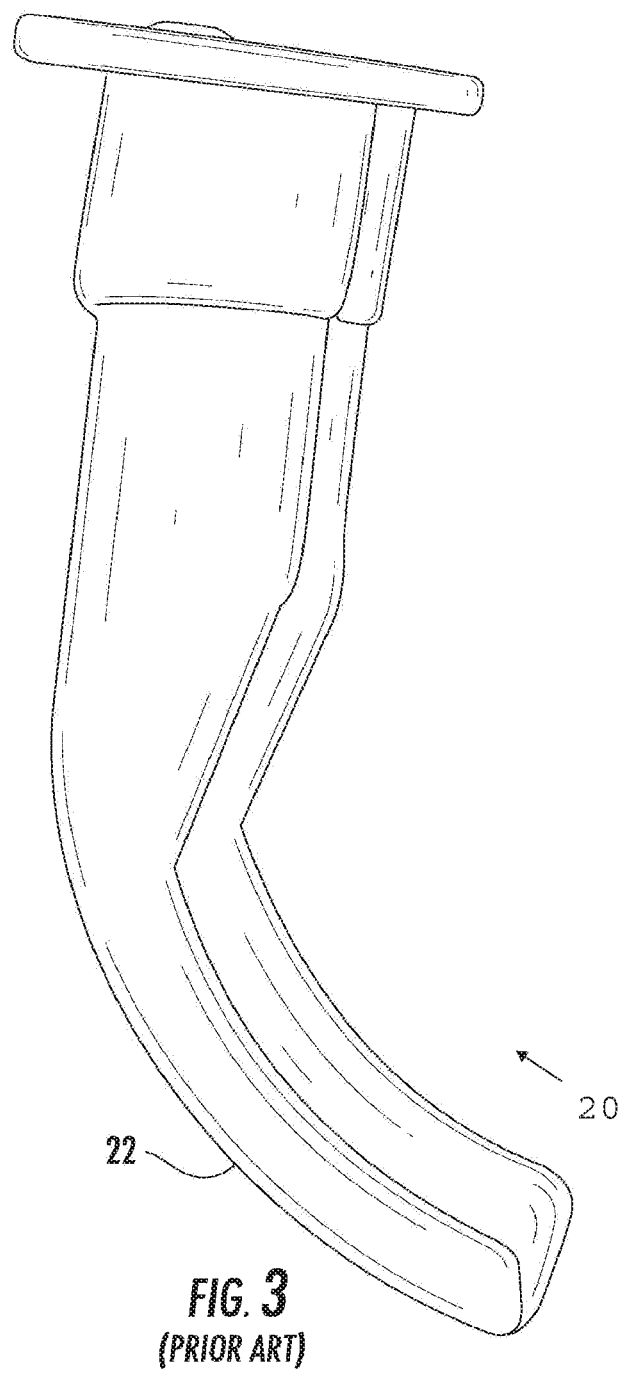
FIG. 3 is a perspective view of the side of a commercially available oral airway that is believed to be representative of the Williams oral airway.
Figure 4:
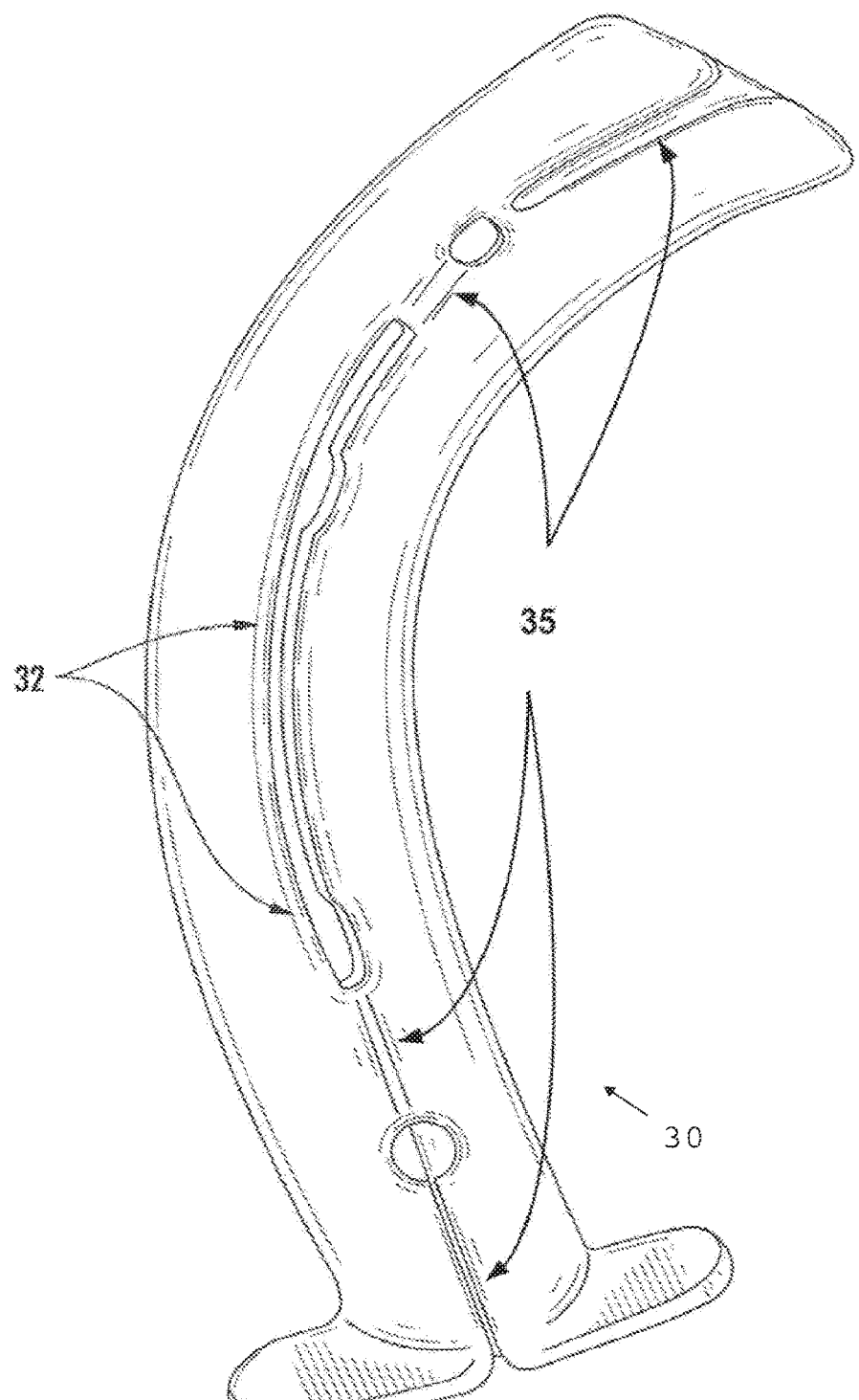
FIG. 4 is a perspective view of the side of a commercially available oral airway that is believed to be representative of the Berman oral airway.

Turning now to FIGS. 1-4, commercially available oral airways are illustrated. In particular, FIGS. 1-2 illustrate the Ovassapian oral airway; FIG. 3 illustrates the Williams oral airway; and FIG. 4 illustrates the Berman oral airway, all of which are commercially available and are described in detail in the "background of the invention" section above.

Figure 5:
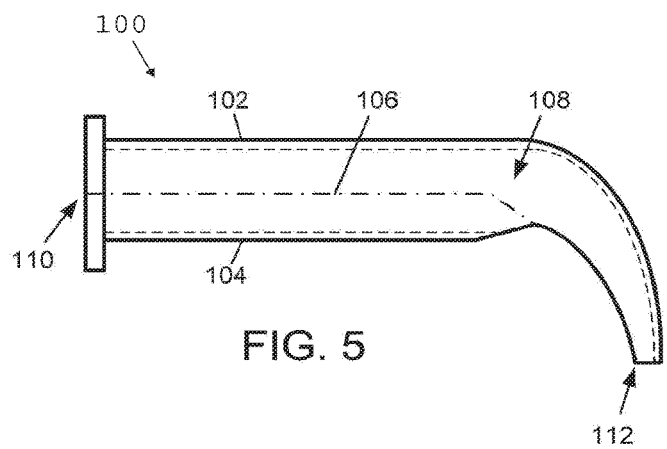
FIG. 5 is a side elevational view of an oral airway 100 in accordance with a preferred embodiment of the invention.
Figure 6:
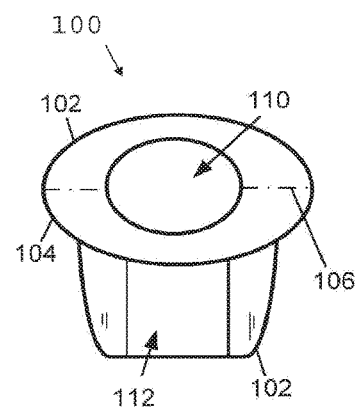
FIG. 6 is a perspective view generally of a front of the oral airway 100 of FIG. 5.
Figure 7:
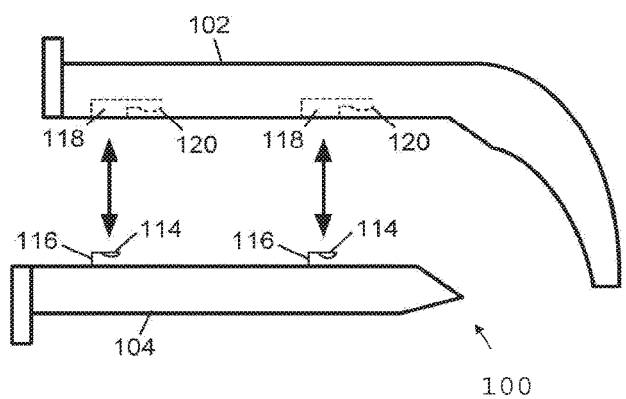
FIG. 7 is a side elevational view of the oral airway 100 of FIG. 5 illustrating the separation of two components that form the oral airway 100.
Figure 8:
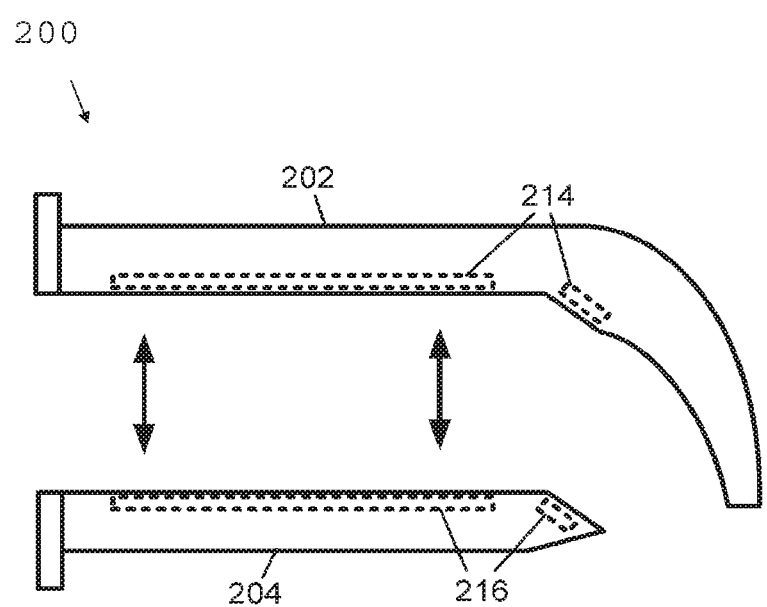
FIG. 8 is a side elevational view of another oral airway 200 in accordance with another preferred embodiment of the invention illustrating the separation of two components that form the oral airway 200.
Figure 9:
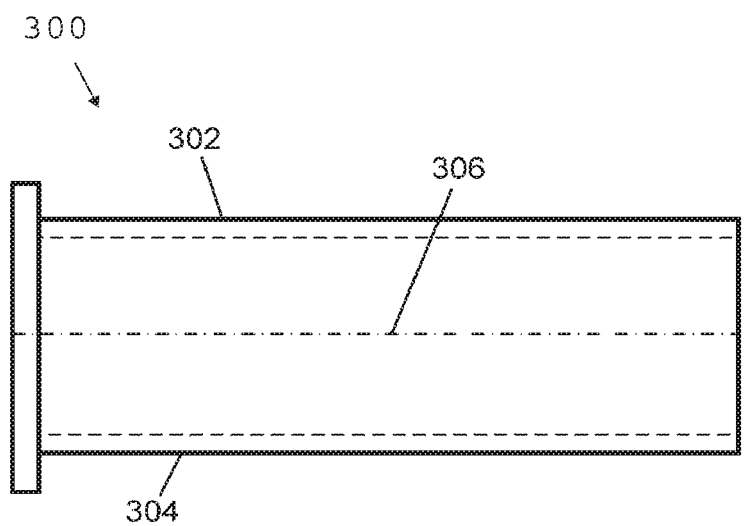
FIG. 9 is a top elevational view of an oral airway 300 in accordance with yet another preferred embodiment of the invention.
Figure 10:
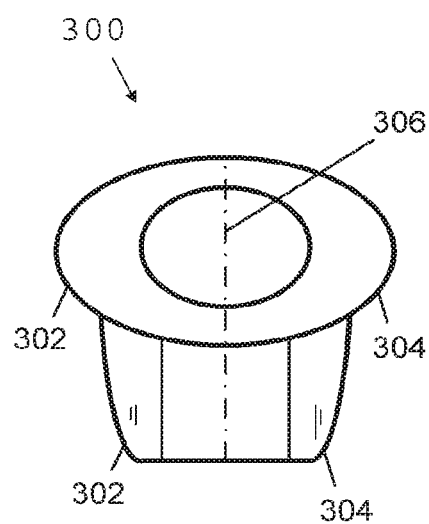
FIG. 10 is a perspective view generally of a front of the oral airway 300 of FIG. 9.
Figure 11:
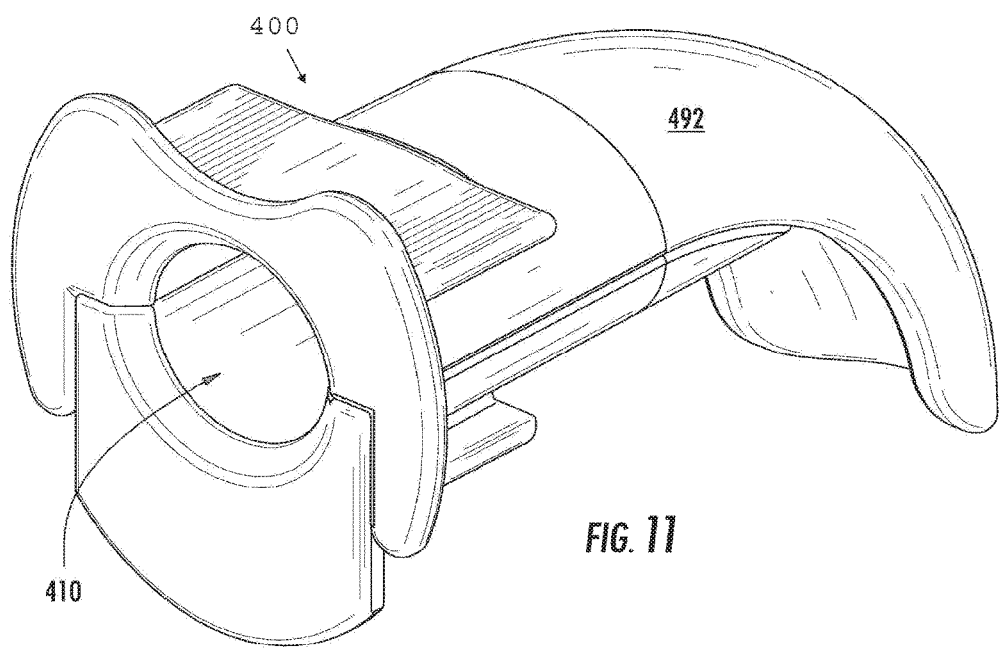
FIG. 11 is an isometric view of an oral airway 400 in accordance with yet another preferred embodiment of the invention.

In contrast, oral airways in accordance with preferred embodiments of the invention are illustrated in FIGS. 5-10. In particular, FIGS. 5-7 illustrate an oral airway 100 in accordance with a first preferred embodiment of the invention; FIG. 8 illustrates an oral airway 200 in accordance with a second preferred embodiment of the present invention; FIGS. 9 and 10 illustrate an oral airway 300 in accordance with a third preferred embodiment of the invention; and FIGS. 11-35 illustrate an oral airway 400, or components thereof, in accordance with a fourth embodiment of the invention.

As shown in FIGS. 5 and 6, the oral airway 100 includes a first component 102 and a second component 104 that are removably coupled together to form the oral airway 100. A dashed line 106 is included in FIG. 5 to demarcate a preferred juncture between the first component 102 and the second component 104. The demarcation line 106 also extends in similar fashion about the other side of the oral airway 100. The first component 102 extends over the second component 104 and forms the "top" of the oral airway 100, with the second component 104 forming the "bottom" of the oral airway 100. When coupled together, the first component 102 and the second component 104 define a conduit 108 having a first opening 110 and a second opening 112 through which a fiber-optic scope and an endotracheal tube may be extended for intubation of the trachea.

The first component 102 and the second component 104 are shown decoupled from one another in FIG. 6. When so disengaged, each of the components 102,104 may be independently removed from the mouth of a patient without disrupting the proper placement of an endotracheal tube in the trachea of a patient.

When coupled together, the first component 102 and the second component 104 preferably are forcibly retained in this condition until some minimum amount of force is applied to separate the components 102,104. In the oral airway 100, detents 114 are utilized to retain the coupling between the two components 102,104. In this regard, the detents are formed on elastic, spring-like lever arms 116 that extend from and form part of the second component 104 and that are received within corresponding slots 118 formed in sidewalls of the first component 102. The detents 114 are received and retained by corresponding depressions 120 formed in the slots 118 of the first component 102.

The oral airway 200 of FIG. 8 includes a first component 202 and a second component 204 that are removably coupled together to form the oral airway 200, and is generally similar in design to the oral airway 100 of FIGS. 5-7. The differences between the oral airway 100 and the oral airway 200 relate to the mechanism that is utilized to retain the first and second components 102,104 and 202,204 in their respective coupled disposition. In this regard, while the oral airway 100 of FIGS. 5-7 utilizes an interlocking mechanical structure, including elastic elements, to maintain the components 102,104 in their coupled disposition, the oral airway 200 of FIG. 8 utilizes magnetism to maintain the coupling. Specifically, sidewalls of the first component 202 include magnetized elements 214 and sidewalls of the second component 204 of the oral airway 200 include magnetized elements 216 that respectively attract each other when the two components 102,104 are coupled together.

In various alternative designs of the preferred embodiments, the juncture of the first component and the second component could extend along the top and bottom of the oral airway such that the oral airway splits into two halves wherein, for example, each half is a mirror image of the other. One such example of such an arrangement is shown in FIGS. 9 and 10, wherein an oral airway 300 includes a first component 302 and a second component 304 that are removably coupled together to form the oral airway 300. This oral airway 300 is generally similar in design to the oral airway 100 of FIGS. 5-7 or the oral airway 200 of FIG. 8, except that the two components 302,304 are joined along a vertical juncture, demarcated by a dashed line 306 as shown in FIGS. 9 and 10, rather than by a horizontal juncture such as, for example, the juncture demarcated by dashed line 106 in FIG. 5.

Other configurations are within the scope of the invention, with the common feature being that the oral airway separates into two independent pieces such that the oral airway may be removed directly away from the sides an endotracheal tube without displacement of the endotracheal tube. In other words, when coupled, the two components preferably completely encompass or encircle an endotracheal tube extended through the conduit of the oral airway and, when decoupled, the two components preferably do not completely encompass or encircle an endotracheal tube such that each component may be independently removed away from the endotracheal tube.

Figure 12:
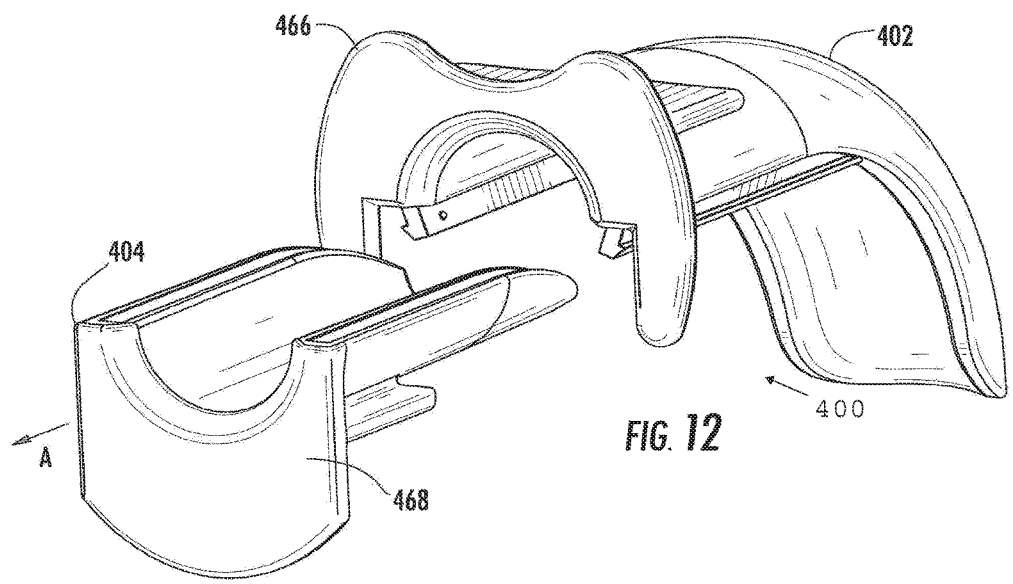
FIG. 12 is an exploded perspective view of the oral airway 400 of FIG. 11.
Figure 13:
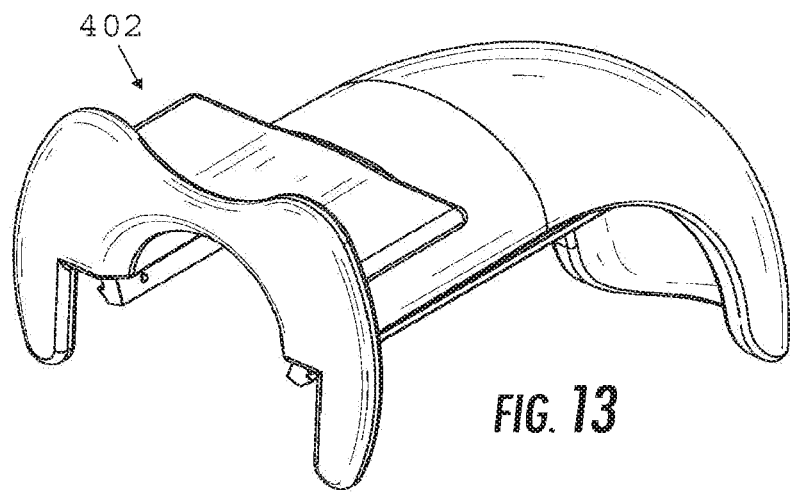
FIG. 13 is an isometric view of a first component 402 of the oral airway of FIG. 11.
Figure 14:
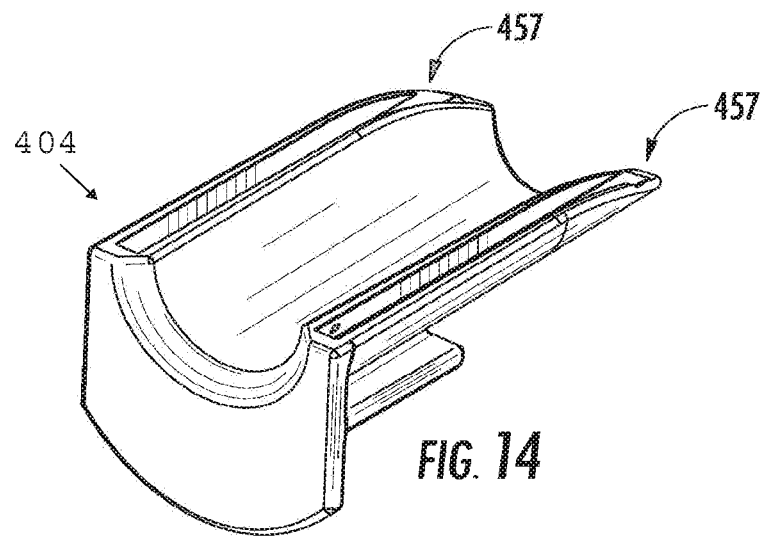
FIG. 14 is an isometric view of a second component 402 of the oral airway of FIG. 11.
Figure 15:
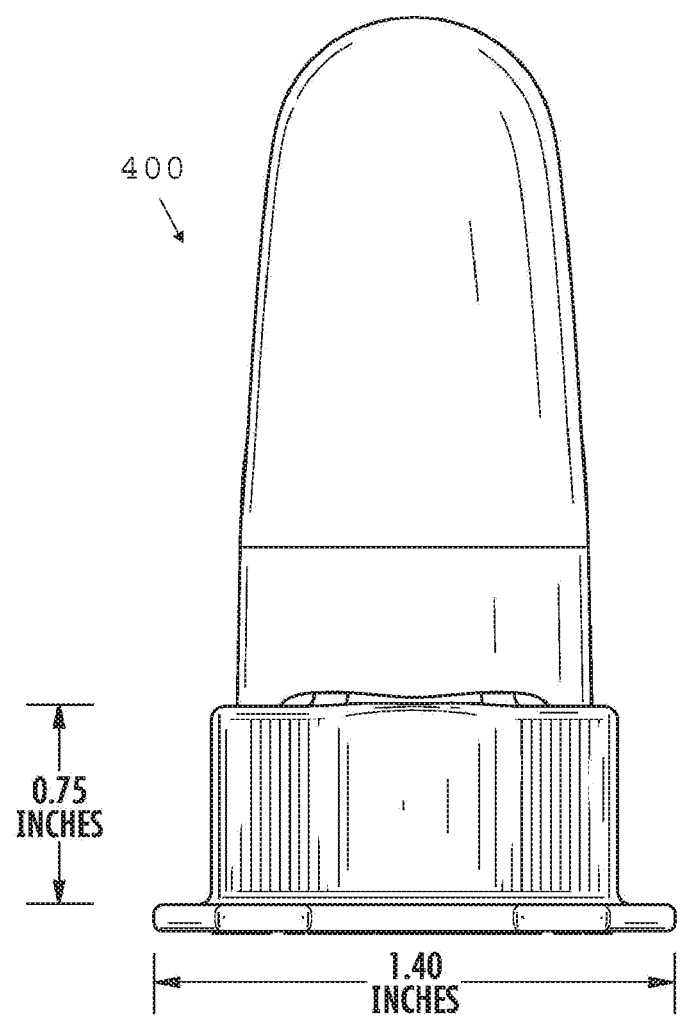
FIG. 15 is a top plan view of the oral airway 400 of FIG. 11.
Figure 17:
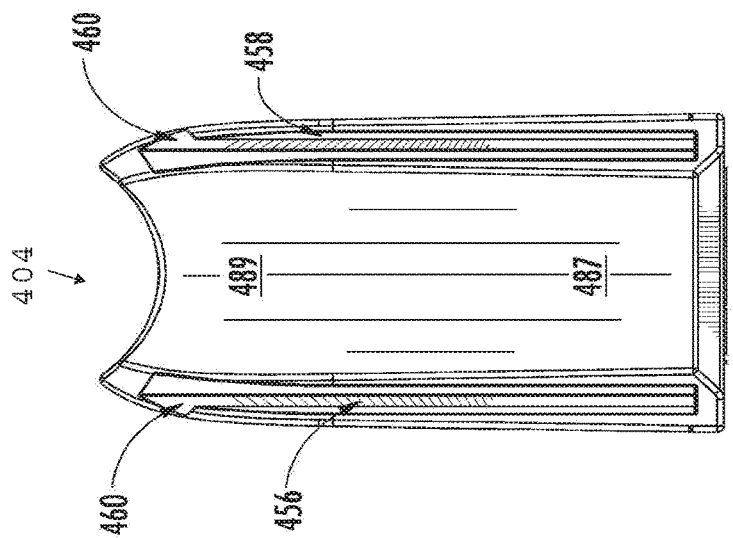
FIG. 17 is a top plan view of the second component 404 of the oral airway of FIG. 11.
Figure 16:
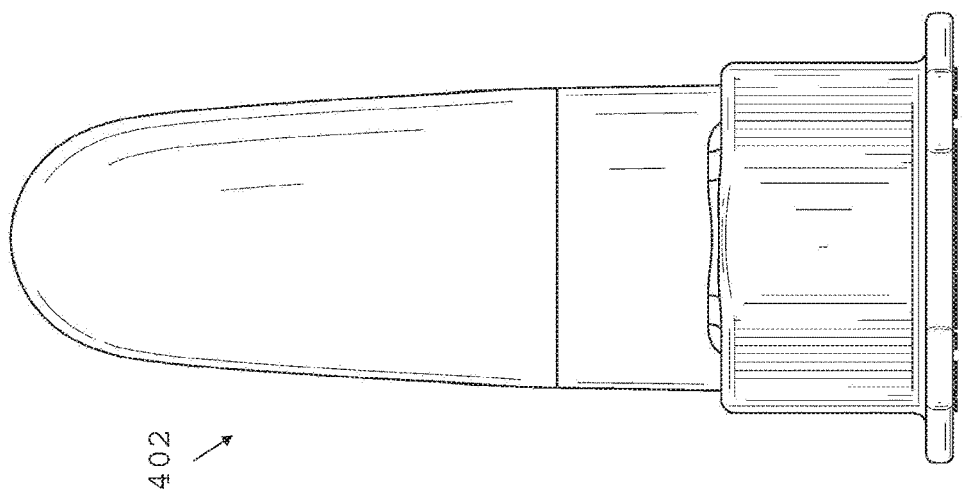
FIG. 16 is a top plan view of the first component 402 of the oral airway of FIG. 11.

Yet another oral airway 400—and components thereof—in accordance with a preferred embodiment of the invention collectively are illustrated in FIGS. 11-35. In particular, FIGS. 11, 15, 18, 21, 24, 27, 30, and 33 illustrate various views of the first component 402 and second component 404 removably coupled together to form the oral airway 400. FIGS. 13, 16, 19, 22, 25, 28, and 31 illustrate various corresponding views of the first component 402, and FIGS. 14, 17, 20, 23, 26, 29 and 32 likewise illustrate various corresponding views of the second component 404. FIG. 12 illustrates an exploded view of the first component 402 and second component 404 arrived at by decoupling and sliding of the second component 404 in the direction of arrow A relative to the first component 402. FIGS. 34 and 35 illustrate partial views of the oral airway 400 focusing on corresponding elements of the latch mechanism of the oral airway 400.

When the first component 402 and second component 404 are removably coupled together to form the oral airway 400, the first component 402 extends over the second component 404 and forms the "top" of the oral airway 400, with the second component 404 forming the "bottom" of the oral airway 400. As such, the first component 402 sometimes may be referred to herein as the "superior" component and the second component 404 sometimes may be referred to herein as the "superior" component 404.

Figure 30:
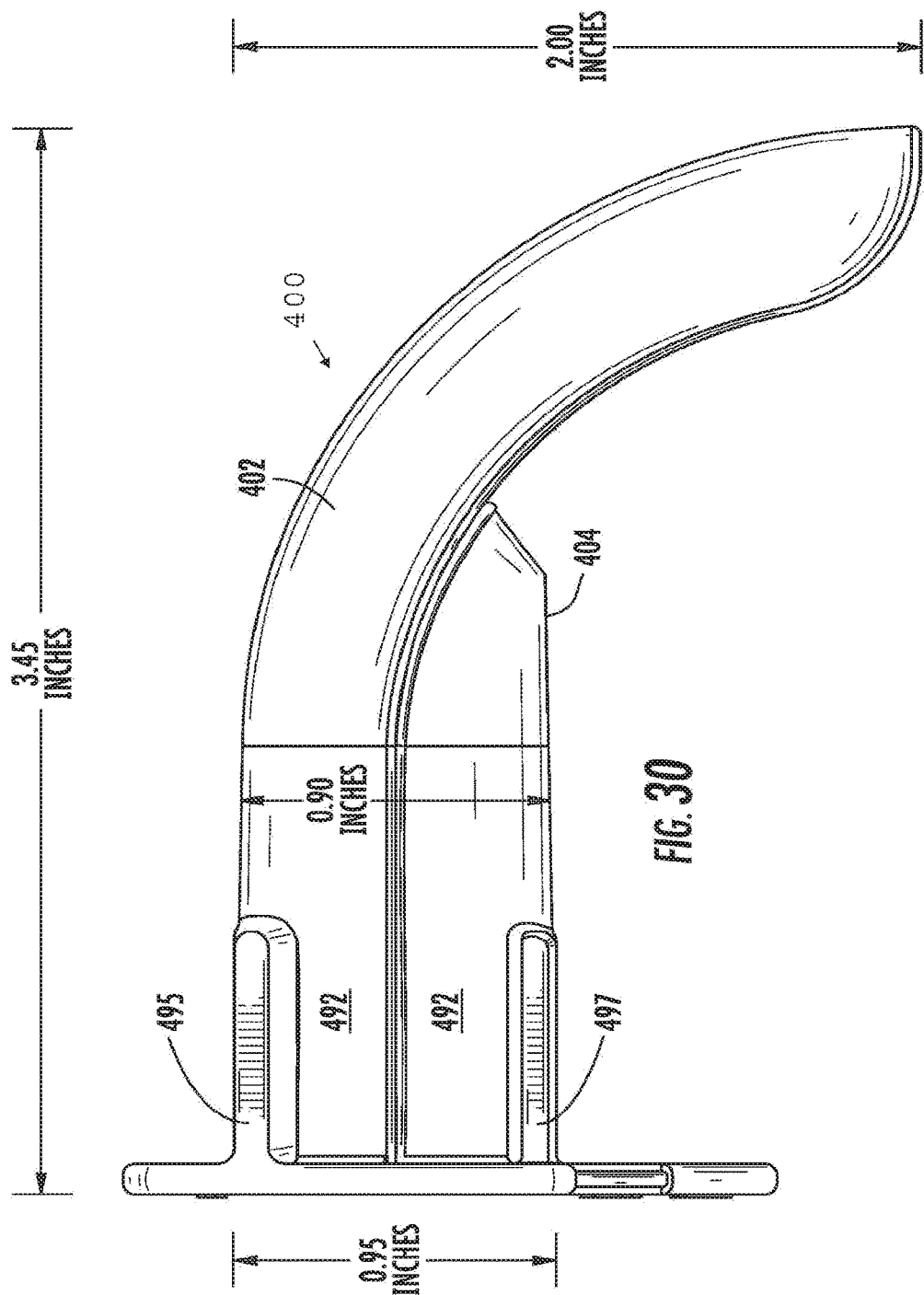
FIG. 30 is second side elevational view of the oral airway 400 of FIG. 11.

Furthermore, when coupled together, the first component 402 and the second component 404 collectively define a conduit 408 (FIG. 21) having a first opening 410 (FIG. 11) and a second opening 412 (FIG. 18) through which, for example, a fiber-optic scope and/or an endotracheal tube may be extended for intubation of the trachea. Preferably, the internal dimension of the conduit is maximized in order to accommodate sizes of endotracheal tubes that are larger than what conventional oral airways will accommodate. Preferred dimensions for a size#9 (90 mm) oral airway are identified in the drawings and, in particular, FIGS. 21, 22, 23, and 30. The internal diameter in this illustrated embodiment is approximately 0.9 inches at the first and second portions of the first component 402 as shown in FIG. 30.

The first component 402 and the second component 404 also are forcibly retained in this condition until some minimum amount of force is applied to separate the components 402,404. Specifically, an interlocking mechanical structure is utilized in the oral airway 400 to retain the coupling between the two components 402,404. The first component 402 includes a first elongate tongue 452 (FIG. 19) and a second elongate tongue 454 (FIG. 19) extending in generally parallel relation. The second component 404 includes a first elongate groove 456 (FIG. 17) and a second elongate groove 458 (FIG. 17) extending in generally parallel relation. When the first and second components 402,404 are removably coupled together, the first and second tongues 452,454 extend, respectively, within the first and second grooves 456,458. Specifically, each tongue 452,454 includes a leading end 453 (FIG. 19) and a trailing end 455 (FIG. 19); each groove 456,458 includes an opening 460 (FIG. 17) at a forward end 457 (FIG. 14) for receiving the leading end 453 of a respective tongue 452,454 therethrough; and, when the first and second components 402,404 are removably coupled together, the elongate tongues 452,454 are received respectively within the elongate grooves 456,458.

Each tongue 452,454 further includes a raised bump or protuberance 462 (FIG. 35) proximate the leading end 453; each groove 456,458 further includes an indentation or recess 464 (FIG. 34) located proximate the rear end 459; and, when the first and second components 402,404 are removably coupled together, each protuberance 462 is received within a recess 464 for latching of the first and second components 402,404 in physical engagement with one another.

Each tongue 452,454 includes a cross-sectional profile that closely corresponds to a cross-sectional profile of a groove 456,458 for close fitting of the tongue 452,454 within the groove 456,458 without undesired play.

The oral airway 400 also includes a mouth guard for abutting an exterior area of the mouth of a patient during endotracheal intubation and preventing the oral airway 400 from overextending into the mouth of the patient. In particular, the first component 402 forms a first mouth guard portion 466 (FIG. 12) and the second component 404 forms a second mouth guard portion 468 (FIG. 12), with the first mouth guard portion 466 and the second mouth guard portion 468 defining the mouth guard itself. The first component 402 and the second component 404 also preferably define a chamfer 470 (FIG. 21) between the conduit 408 and an exterior surface of the mouth guard for facilitating the introduction of a fiber-optic scope or an endotracheal tube.

Figure 18:
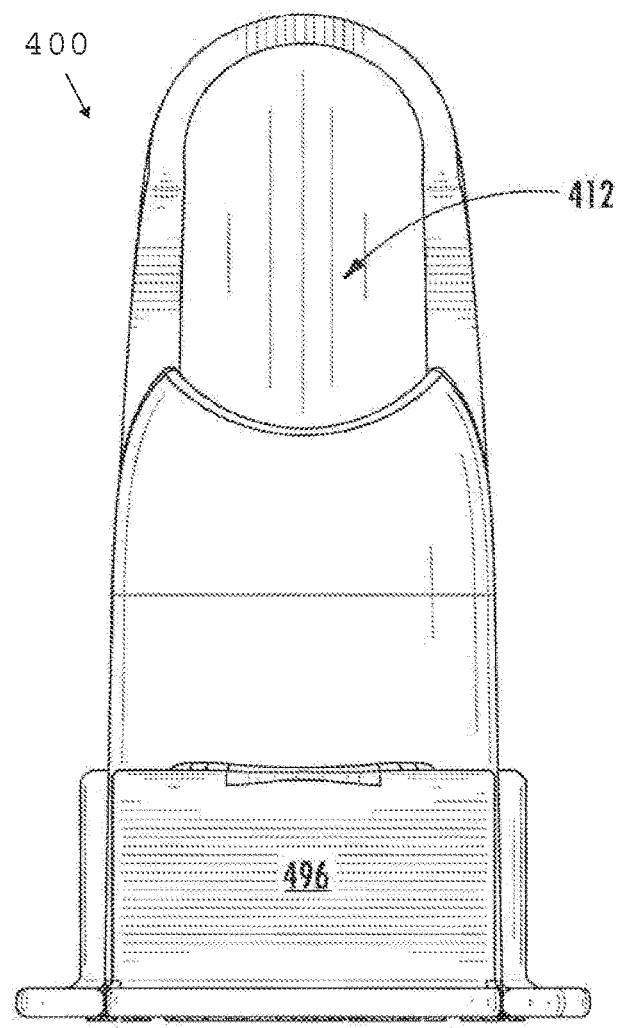
FIG. 18 is a bottom plan view of the oral airway 400 of FIG. 11.
Figure 21:
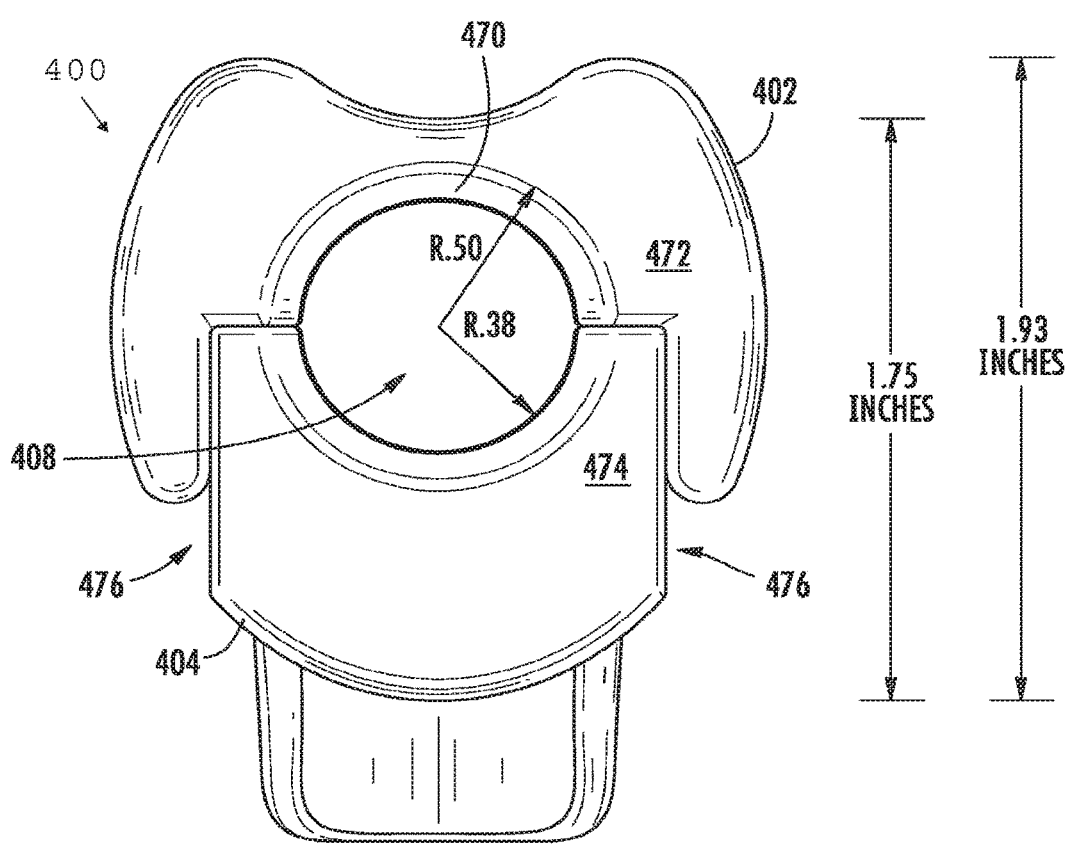
FIG. 21 is a front elevational view of the oral airway 400 of FIG. 11.
Figure 23:
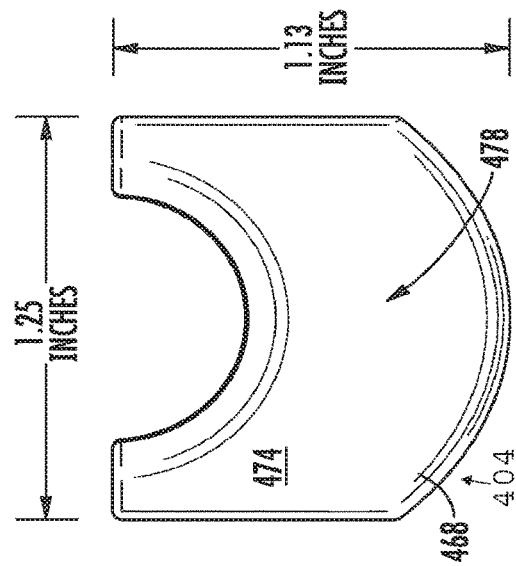
FIG. 23 is a front elevational view of the second component 404 of the oral airway of FIG. 11.
Figure 22:
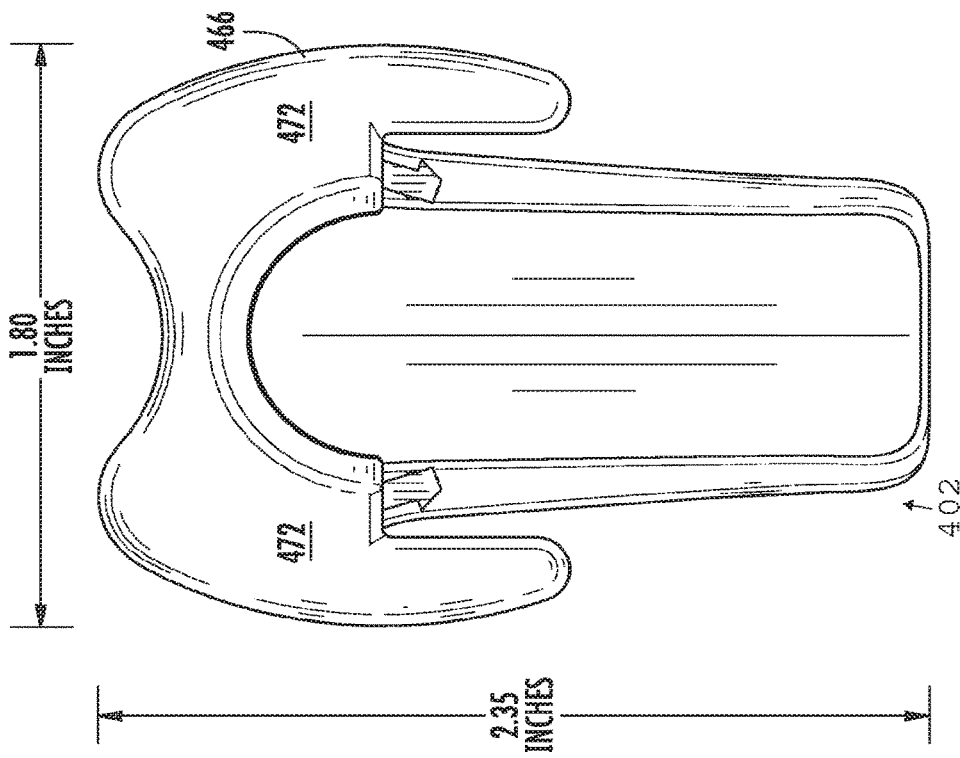
FIG. 22 is a front elevational view of the first component 402 of the oral airway of FIG. 11.
Figure 24:
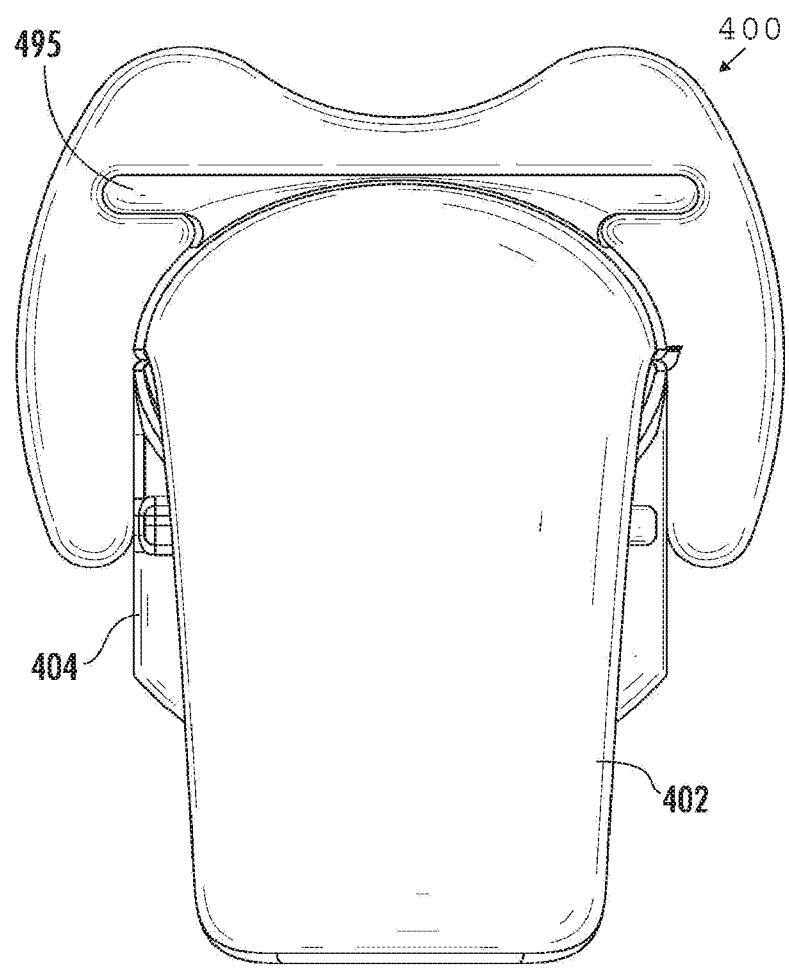
FIG. 24 is a rear elevational view of the oral airway 400 of FIG. 11.

The first mouth guard portion 466 and the second mouth guard portion 468 each have respective surfaces 472,474 (FIG. 21) that extend in generally coplanar relation for presenting a flush exterior mouth guard surface as seen, for example, in FIG. 18. Furthermore, as perhaps best seen in FIG. 21, the first mouth guard portion 466 extends adjacent opposite lateral sides 476 of the second mouth guard portion 468 thereby bracketing the second mouth guard portion 468. The first mouth guard portion 466 may be characterized as generally "M" shaped or "C" shaped, as perhaps best seen in FIG. 22. Moreover, the second mouth guard portion 468 may be characterized as generally "U" shaped, as perhaps best seen in FIG. 23.

The second mouth guard portion 468 also includes an area 478 dimensioned for grasping between a finger and thumb of a hand for decoupling of the first and second components 402,404. This area 478 preferably comprises a pull-tab and corresponds to, at least to some extent if not completely, the second mouth guard portion 468.

With specific regard to the first component 402, the first component 402 includes an anterior portion 480 (FIG. 28) and a posterior elbow portion 482 (FIG. 28). The anterior portion 480 extends generally linearly in a longitudinal direction along a first extent and includes a first curved surface 481 (FIG. 19). The posterior elbow portion 482 extends generally curvilinearly in the longitudinal direction and includes a second curved surface 483 (FIG. 19) that defines a posterior curve 485 (FIG. 28). Furthermore, the second curved surface 483 of the posterior elbow portion 482 and the first curved surface 481 of the anterior portion 480 together define a first, superior guiding surface of the oral airway 400.

Likewise, with specific regard to the second component 404, the second component 404 also has a first portion 486 (FIG. 29) and a second portion 488 (FIG. 29). The first portion 486 extends generally linearly in the longitudinal direction approximately the first extent and includes a first curved surface 487 (FIG. 17) located in opposing relation to the first curved surface 481 of the anterior portion 480 of the first component 402. The second portion 488 includes a second curved surface 489 (FIG. 17) located in opposing relation to the second curved surface 483 of the posterior elbow portion 482 of the first component 402. The second portion 488 of the second component 404 also includes tapering side edges 490 (FIG. 29). The second curved surface 489 of the second portion 488 of the second component 404 and the first curved surface 487 of the first portion 486 of the second component 404 together define a second, inferior guiding surface of the oral airway 400.

As will be appreciated from the drawings, the superior guiding surface and the inferior guiding surface together define and encompass an interior passage (i.e., conduit 408) through the oral airway 400. This interior passage preferably is dimensioned to direct a fiber-optic scope or an endotracheal tube extending through the interior passage for tracheal intubation. As shown by the cross-sectional view of FIG. 33, the interior passage is generally oval in cross-sectional profile as indicated at 491 and, specifically, is generally circular in cross-sectional profile.

Figure 33:
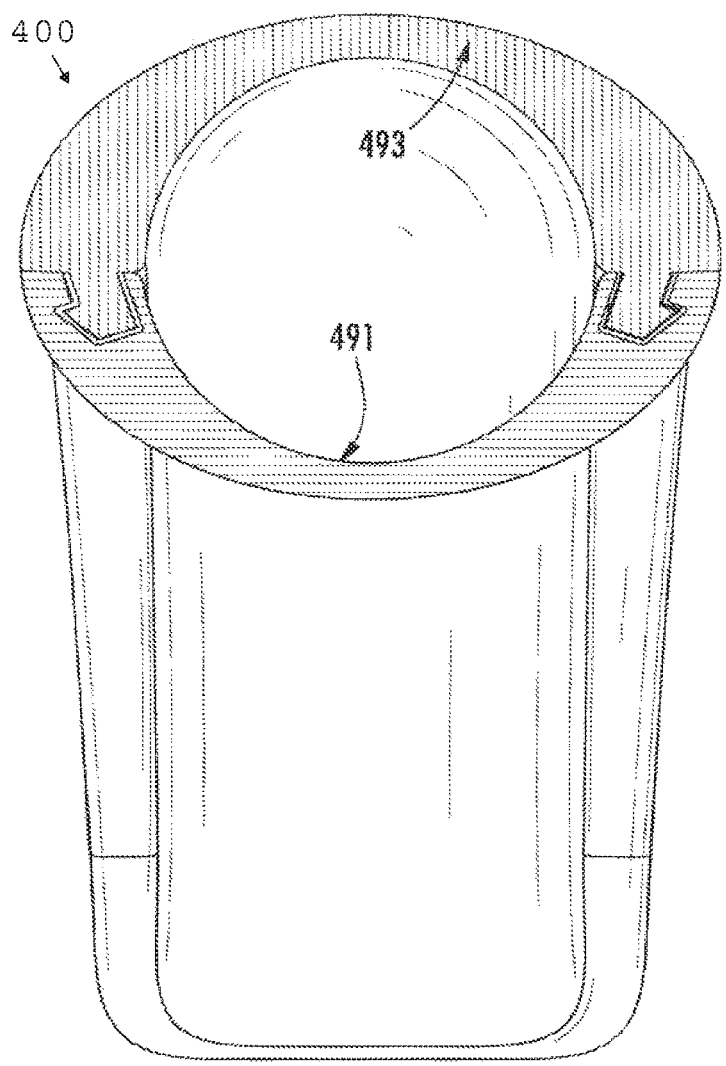
FIG. 33 is a first side elevational view of the oral airway 400 taken along lines 33 in FIG. 27.

With continuing reference to FIG. 33, the first and second components 402,404 include a continuous, uninterrupted curved outer exterior surface 492 (FIG. 27) that circumferentially surrounds the interior passage, and this exterior surface 492 is generally oval in cross-sectional profile as indicated at 493 in FIG. 33.

The first component 402 of the oral airway 400 also includes a first generally planar member 495 (FIG. 24) that protracts in opposite lateral directions from the exterior surface 492 of the anterior portion 480 of the first component 402. Likewise, the second component 404 includes a second generally planar member 497 (FIG. 26) that protracts in opposite lateral directions from the exterior surface 492 of the first portion 486 of the second component 404. The first generally planar member 495 and the second generally planar member 497 extend in spaced parallel relation to one another and are configured to splint the teeth of the mouth of a patient and provide stability against rotation or wobbling of the oral airway 400 during endotracheal intubation. The second generally planar member 497 also includes a flat lingual surface 496 (FIG. 18) that is configured to forwardly depress the tongue of a patient during endotracheal intubation.

In use of any of the foregoing oral airways, a method of tracheal intubation includes the steps of extending a fiber-optic scope or an endotracheal tube through a conduit defined by first and second components of an oral airway, wherein the first and second components are removably coupled together to define the conduit; decoupling the first and second components after an endotracheal tube has been extended through the conduit for tracheal intubation such that the first and second components are physically separated from one another; removing the first component from the patient's mouth without disrupting the endotracheal tube; and removing the second component from the patient's mouth without disrupting the endotracheal tube. The step of decoupling the first and second components includes sliding one of the components relative to the other of the components. The step of decoupling the first and second components comprises further applying a sufficient amount of force to overcome a latch that serves to retain the first and second components together in fixed disposition. When decoupled, each of the components may be independently removed from the mouth of a patient without disrupting the proper placement of an endotracheal tube in the trachea of the patient. With reference to the oral airway 400, the inferior component 404 preferably is removed and then the superior component 402 is removed.

Returning now to consideration of all of the illustrated embodiments of the drawings, preferably the walls of the components 102,104 of oral airway 100, the walls of the components 202,204 of oral airway 200, the walls of the components 302,304 of oral airway 300, and the walls of the components 402,404 of oral airway 400 are constructed from medical grade low density polyethylene and have sufficient rigidity—or are reinforced—so as to prevent collapse when the oral airway is bitten down upon by a patient. The oral airways also preferably are latex free.

Oral airways in accordance with preferred embodiments of the invention may be produced in a variety of sizes ranging from neonatal to large adult sizes. As such, the oral airways preferably are color coded so as to indicate size upon quick visual observation.

Additionally and/or alternatively, an oral airway in accordance with the present invention may be adapted, configured, or manufactured to provide a desirable smell and/or taste. For example, a flavoring material may be applied during the manufacture of the oral airway, or may be applied afterwards, that results in a desirable flavor being experienced when the oral airway is utilized in the mouth. The flavor may be, for example, that of a food, a natural flavor, or an artificial flavor including, but not limited to, bubble gum or a fruit, such as an orange. Alternatively, or in addition, a material may be may be applied during the manufacture of the oral airway, or may be applied afterwards, that results in a desirable scent or odor being experienced when the oral airway is utilized. The scent or odor may be that of a food or other pleasant item. In connection with the flavoring and/or scent, the oral airway may include a corresponding color, such as a pink color if the flavoring and/or scent is that of bubble gum.

Based on the foregoing description, it will be readily understood by those persons skilled in the art that the invention is susceptible of broad utility and application. Many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention.

Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof.

What is claimed is:

1. An oral airway, comprising:
   (a) a first individual component having a first curved guiding surface; and
   (b) a second individual component removably coupled together with the first component, the second component having a second curved guiding surface located in opposing relation to the first guiding surface;
   (c) wherein, when the first and second components are coupled together, the first curved guiding surface and the second curved guiding surface each substantially define half of a perimeter of a collectively defined interior passage extending through the oral airway for directing a fiber-optic scope or an endotracheal tube through the oral airway, but when the first and second components are decoupled, no passage is defined by either the first component or the second component;
   (d) wherein the first component and the second component are configured to be removably coupled together in interlocking engagement; and
   (e) wherein, when the first component and the second component are coupled together, the first component and the second component are separable by sliding longitudinally, relative to each other, out of complete physical engagement with one another along a lengthwise axis of the interior passage.

2. The oral airway of claim 1, wherein each of the first and second guiding surfaces comprises continuous, uninterrupted surfaces.

3. The oral airway of claim 1, wherein the interior passage has a generally oval cross-section.

4. The oral airway of claim 1, wherein the first component has an anterior portion extending generally linearly in a longitudinal direction a first extent and a posterior elbow portion that directs a fiber-optic scope or endotracheal tube anteriorly toward the vocal cords during tracheal intubation.

5. The oral airway of claim 1, wherein the first component and the second component comprise continuous, generally uninterrupted interior surfaces that collectively encompass and define the interior passage.

6. The oral airway of claim 1, wherein the first component and the second component collectively provide a continuous, generally uninterrupted exterior surface circumferentially surrounding the interior passage.

7. The oral airway of claim 1, wherein the first component further includes a posterior curve that directs a fiber-optic scope or endotracheal tube anteriorly toward vocal cords during tracheal intubation.

8. The oral airway of claim 1, wherein the first component extends over and on opposites sides of the second component when the first component and the second component are removably coupled together, and wherein the first component further comprises a mouth guard for abutting an exterior area of a mouth of a patient during endotracheal intubation and preventing the oral airway from overextending into the mouth of the patient.

9. The oral airway of claim 1, wherein the first component and the second component define a mouth guard of the oral airway when the first component and the second component are removably coupled together, the first component forming a first mouth guard portion and the second component forming a second mouth guard portion, with the first mouth guard portion and the second mouth guard portion defining the mouth guard.

10. The oral airway of claim 1, wherein the first component includes a first generally planar member protracting in opposite lateral directions from the exterior surface of the first portion of the first component; wherein the second component includes a second generally planar member protracting in opposite lateral directions from the exterior surface of the first portion of the second component, the first generally planar member and the second generally planar member extending in spaced parallel relation to one another; and wherein the first generally planar member and the second generally planar member are configured to splint teeth of a mouth of a patient, and provide stability against rotation of the oral airway, during endotracheal intubation.

11. The oral airway of claim 1, wherein at least one of the first component and the second component comprises a flavoring material that results in a particular flavor being experienced when the oral airway is utilized in a mouth of a patient.

12. The oral airway of claim 1, wherein at least one of the first component and the second component comprises material that results in a particular scent or odor being experienced when the oral airway is utilized.

13. An oral airway, comprising first and second individual components that are configured to be removably coupled together, wherein:
   (a) the first component has,
      (i) an anterior portion extending generally linearly in a longitudinal direction, the anterior portion including a first curved surface, and
      (ii) a posterior elbow portion including a second curved surface, the second curved surface of the posterior elbow portion in combination with the first curved surface of the anterior portion defining a first curved guiding surface; and
   (b) the second component has,
      (i) a first portion extending generally linearly in the longitudinal direction, the first portion of the second component including a first curved surface located in opposing relation to the first curved surface of the anterior portion of the first component, and
      (ii) a second portion including a second curved surface located in opposing relation to the second curved surface of the posterior elbow portion of the first component, the second curved surface of the second portion of the second component in combination with the first curved surface of the first portion of the first component defining a second curved guiding surface;
   (c) wherein, when the first and second components are coupled together, the first curved guiding surface and the second curved guiding surface each substantially define half of a perimeter of a collectively defined interior passage through the oral airway for directing a fiber-optic scope or an endotracheal tube through the oral airway, but the first and second components are configured such that, when decoupled from one another, no passage is defined; and
   (d) wherein, when the first component and the second component are coupled together, the first component and the second component are separable by sliding longitudinally, relative to each other, out of complete physical engagement with one another along a lengthwise axis of the interior passage.

14. The oral airway of claim 13, wherein the interior passage has a generally oval cross-section in an area defined by the anterior portion of the first component and the first portion of the second component.

15. A method comprising the steps of:
   (a) providing an oral airway comprising,
      (i) a first individual component having an interior curved first guiding surface, and
      (ii) a second individual component having an interior curved second guiding surface,
      (iii) wherein, when the first and second components are coupled together, the first curved guiding surface and the second curved guiding surface each substantially define half of a perimeter of a collectively defined interior passage extending through the oral airway for directing a fiber-optic scope or an endotracheal tube through the oral airway, but when the first and second components are decoupled, no passage is defined, and
      (iv) wherein, when the first and second components are coupled together, the first component and the second component are separable by sliding longitudinally, relative to each other, out of complete physical engagement with one another along a lengthwise axis of the interior passage;
   (b) locating the oral airway within a mouth of a patient;
   (c) extending an elongate member through the interior passage defined by the first and second components of the oral airway;
   (d) decoupling the first and second individual components, after the elongate member has been extended through the interior passage of the oral airway, such that the first and second components are physically separated from one another;
   (e) removing the first component from the patient's mouth without disrupting the elongate member; and
   (f) removing the second component from the patient's mouth without disrupting the elongate member.

16. The method of claim 15, wherein the first and second components completely surround circumferentially the elongate member when extended through the interior passage of the oral airway.

17. The method of claim 15, wherein the elongate member comprises an endotracheal tube or a fiber-optic scope.

* * * * *